US008716301B2

(12) United States Patent
Sitkovsky et al.

(10) Patent No.: US 8,716,301 B2
(45) Date of Patent: May 6, 2014

(54) METHODS FOR USING EXTRACELLULAR ADENOSINE INHIBITORS AND ADENOSINE RECEPTOR INHIBITORS TO ENHANCE IMMUNE RESPONSE AND INFLAMMATION

(75) Inventors: Michail V. Sitkovsky, Bethesda, MD (US); Akio Ohta, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 68 days.

(21) Appl. No.: 13/310,264

(22) Filed: Dec. 2, 2011

(65) Prior Publication Data

US 2012/0093856 A1 Apr. 19, 2012

Related U.S. Application Data

(62) Division of application No. 10/498,416, filed as application No. PCT/US02/36829 on Nov. 14, 2002, now Pat. No. 8,080,554.

(60) Provisional application No. 60/340,772, filed on Dec. 12, 2001, provisional application No. 60/342,585, filed on Dec. 19, 2001.

(51) Int. Cl.
*A61K 31/522* (2006.01)
*A61K 31/53* (2006.01)

(52) U.S. Cl.
USPC ............... 514/263.34; 514/245; 514/247

(58) Field of Classification Search
USPC .................... 514/263.34, 245, 247
See application file for complete search history.

(56) References Cited

U.S. PATENT DOCUMENTS

| | | | |
|---|---|---|---|
| 5,391,568 | A | 2/1995 | Chung |
| 5,543,508 | A | 8/1996 | Haseloff et al. |
| 5,545,627 | A | 8/1996 | Jacobson et al. |
| 5,814,667 | A | 9/1998 | Mitchell et al. |
| 5,859,019 | A | 1/1999 | Liang et al. |
| 6,147,878 | A | 11/2000 | Heselton |
| 6,180,133 | B1 | 1/2001 | Quan et al. |
| 6,316,435 | B2 | 11/2001 | Byrd et al. |
| 2001/0022980 | A1 | 9/2001 | Bell et al. |

FOREIGN PATENT DOCUMENTS

| | | |
|---|---|---|
| JP | H10-506265 | 6/1998 |
| WO | WO 96/02555 A1 | 2/1996 |
| WO | WO 00/03741 A2 | 1/2000 |
| WO | WO 01/39777 A1 | 6/2001 |

OTHER PUBLICATIONS

Belizario et al., "Caffeine Potentiates the Lethality of Tumour Necrosis Factor in Cancer Cells," *Br. J. Cancer* 67:1229-1235, 1993.
Braun and Ishizuka, "Cyclic AMP and Immune Responses: II. Phosphodiesterase Inhibitors as Potentiators of Polynucleotide Effects on Antibody Formation," *J. Immunol.* 107:1036-1042, 1971.
Webb et al., "Antitumor Effects of Polynucleotides and Theophylline," *Cancer Res.* 32:1814-1819, 1972.
Bandyopadhyay and Poddar, "Theophylline-Induced Changes in Mammalian Adenosine Deaminase Activity and Corticosterone Status: Possible Relation to Immune Response," *Methods Find. Exp. Clin. Pharmacol.* 19:181-184, 1997.
Barcz et al., "Adenosine Receptor Antagonism Causes Inhibition of Angiogenic Activity of Human Ovarian Cancer Cells," *Oncol. Rep.* 7:1285-1291, 2000.
Braun et al., "Immuno Enhancing Effects of Theophylline," *Bacteriol. Proc.* 71:72, 1971.
Byfield et al., "Mice, Men, Mustards, and Methylated Xanthines: The Potential Role of Caffeine and Related Drugs in the Sensitization of Human Tumours to Alkylating Agents," *British J. Cancer* 43:669-683, 1981.
Chen et al., "Neuroprotection by Caffeine and $A_{2A}$ Receptor Inactivation in a Model of Parkinson's Disease," *J. Neurosci.* 21:1-6, 2001.
Chen, "The Adenosine $A_{2A}$ Receptor as an Attractive Target for Parkinson's Disease Treatment," *Drug News Perspect.* 16:597-604, 2003.
Devasagayam and Kesavan, "Radioprotective and Antioxidant Action of Caffeine: Mechanistic Considerations," *Indian J. Exper. Biol.* 34:291-297, 1996.
Gale, "A2a Adenosine Receptors Limit Inflammatory Responses," Reuters Health, Dec. 21, 2001.
Gupta and Zhang, "Angiogenesis: A Curse or Cure?," *Postgrad Med. J.* 81:236-242, 2005.
Hasko et al., "Adenosine Inhibits IL-12 and TNF-α Production via Adenosine $A_{2a}$ Receptor-Dependent and Independent Mechanisms," *FASEB J.* 14:2065-2074, 2000.
Hess, S., "Recent Advances in Adenosine Receptor Antagonist Research," *Expert Opinion on Therapeutic Patents* 11:1533-1561, 2001.
Hoskin et al., "2-Chloroadenosine Inhibits the MHC-Unrestricted Cytolytic Activity of Anti-CD3-Activated Killer Cells: Evidence for the Involvement of a Non-$A_1$/$A_2$ Cell-Surface Adenosine Receptor," *Cell. Immunol.* 159:85-93, 1994.
Hoskin et al., "Adenosine Acts Through an $A_3$ Receptor to Prevent the Induction of Murine Anti-CD3-Activated Killer T Cells," *Int. J. Cancer.* 99:386-395, 2002.
Kalinichenko et al., "Norepinephrine-Mediated Inhibition of Antitumor Cytotoxic T Lymphocyte Generation Involves a β-Adrenergic Receptor Mechanism and Decreased TNF-α Gene Expression," *J. Immunol.* 163:2492-2499, 1999.
Keddie et al., "In vivo characterisation of ZM 241385, a selective adenosine A2A receptor antagonist," *Eur. J. Pharmacol.* 301:107-113, 1996.

(Continued)

*Primary Examiner* — Kevin E Weddington
(74) *Attorney, Agent, or Firm* — Klarquist Sparkman, LLP

(57) ABSTRACT

A method is provided herein to increase an immune response to an antigen. The method includes administering an agent that inhibits extracellular adenosine or inhibits adenosine receptors. Also disclosed are methods to increase the efficacy of a vaccine and to increase an immune response to a tumor antigen or immune cell-mediated tumor destruction.

22 Claims, 13 Drawing Sheets

(56) References Cited

OTHER PUBLICATIONS

Kirkpatrick, "Putting the Brake on Inflammation," *Nature Rev.*, vol. 1, 2002.
Koshiba et al., "Memory of Extracellular Adenosine $A_{2A}$ Purinergic Receptor-mediated Signaling in Murine T Cells," *J. Biol. Chem.* 272:25881-25889, 1997.
MacKenzie et al., "Adenosine Inhibits the Adhesion of Anti-CD3-Activated Killer Lymphocytes to Adenocarcinoma Cells Through an $A_3$ Receptor," *Cancer Res.* 54:3521-3526, 1994.
NIH News Release, "Damping the Flames: Inflammation Control Mechanism Determined," Dec. 19, 2001, National Institutes of Health, Rockville, Maryland.
Nourshargh, "Adenosine Comes Home," *BPS Bulletin*, pp. 5 and 10.
Ohta and Sitkovsky, "Role of G-Protein-Coupled Adenosine Receptors in Downregulation of Inflammation and Protection from Tissue Damage," *Nature* 414:916-920 (2001).
Ohta et al., "A2A Adenosine Receptor Protects Tumors from Antitumor T Cells," *Proc. Natl. Acad. Sci. USA* 103:13132-13137, 2006.
Qin and Blankenstein, "CD4$^+$ T Cell-Mediated Tumor Rejection Involves Inhibition of Angiogenesis that is Dependent on IFNλ Receptor Expression by Nonhematopoietic Cells," *Immunity* 12:677-686, 2000.
Shiozaki et al., "Actions of Adenosine $A_{2A}$ Receptor Antagonist KW-6002 on Drug-Induced Catalepsy and Hypokinesia Caused by Reserpine or MPTP," *Psychopharmacology* 147:90-95, 1999.
Sikora et al., "Cutting Edge: Purinergic Signaling Regulates Radical-Mediated Bacterial Killing Mechanisms in Macrophages Through a $P2X_7$-Independent Mechanism," *J. Immunol.* 163:558-561, 1999.
Slattery et al., "Mouse Interferons: Production by Ehrlich Ascites Tumour Cells Infected with Newcastle Disease Virus and its Enhancement by Theophylline," *J. Gen. Virol.* 49:91-96, 1980.
Sullivan and Linden, Role of $A_{2A}$ Adenosine Receptors in Inflammation, Drug Devel. Res. 45:103-112, 1998.
Sullivan et al., "Neutrophil $A_{2A}$ Adenosine Receptor Inhibits Inflammation in a Rat Model of Meningitis: Synergy with the Type IV Phosphodiesterase Inhibitor, Rolipram," *J. Infect. Dis.* 180:1550-1560, 1999.
Sullivan et al., "Cyclic AMP-Dependent Inhibition of Human Neutrophil Oxidative Activity by Substituted 2-Propynylcyclohexyl Adenosine $A_{2A}$ Receptor Agonists," *Br. J. Pharmacol.* 132:1017-1026, 2001.
Sullivan et al., "$A_{2A}$ Adenosine Receptor Activation Improves Survival in Mouse Models of Endotoxemia and Sepsis," *J. Infect. Dis.* 189:1897-1904, 2004.
Tilley et al., "Mixed Messages: Modulation of Inflammation and Immune Responses by Prostaglandins and Thromboxanes," *J. Clin. Invest.* 108:15-23, 2001.
Toes et al., "CD4 T Cells and their Role in Antitumor Immune Responses," *J. Exp. Med.* 189:753-756, 1999.
Werner and Jolles, "Immunostimulating agents: what next? A review of their present and potential medical applications," *Eur. J. Biochem.* 242:1-19, 1996.
Williams et al., "Adenosine Acts Through a Novel Extracellular Receptor to Inhibit Granule Exocytosis by Natural Killer Cells," *Biochem. Biophys. Res. Commun.* 231:264-269, 1997.
Yu et al., "Selective Inactivation or Reconstitution of Adenosine $A_{2A}$ Receptors in Bone Marrow Cells Reveals their Significant Contribution to the Development of Ischemic Brain Injury," *Nat. Med.* 10:1081-1087, 2004.
Momose et al., "Effects of Intracellular Cyclic AMP Modulators on Human Eosinophil Survival, Degranulation and CD11b Expression," *Int. Arch. Allergy Immunol.* 117:138-145, 1998.
Okubo et al., "Inhibitory Effects of Theophylline and Procaterol on Eosinophil Function," *Intern Med* 36:276-282, 1997.
Wiernik et al., "Phase II Study of Theophylline in Chronic Lymphocytic Leukemia: A Study of the Eastern Cooperative Oncology Group (E4998)," *Leukemia.* 18:1605-1610, 2004.
Slomiński et al., "Assessment of Drug Therapy in Chronic Pulmonary Obstructive Disease," *Pol Merkur Lekarski* 16:133-136, 2004. (English Abstract Only).
Anonymous: "Immunotherapy," thefreedictionary.com, Jun. 3, 2013, pp. 1-2, XP055064941, retrieved from the Internet: URL:http://medical-dictionary.thefreedictionary.com/immunotherapy [retrieved on Jun. 3, 2013].

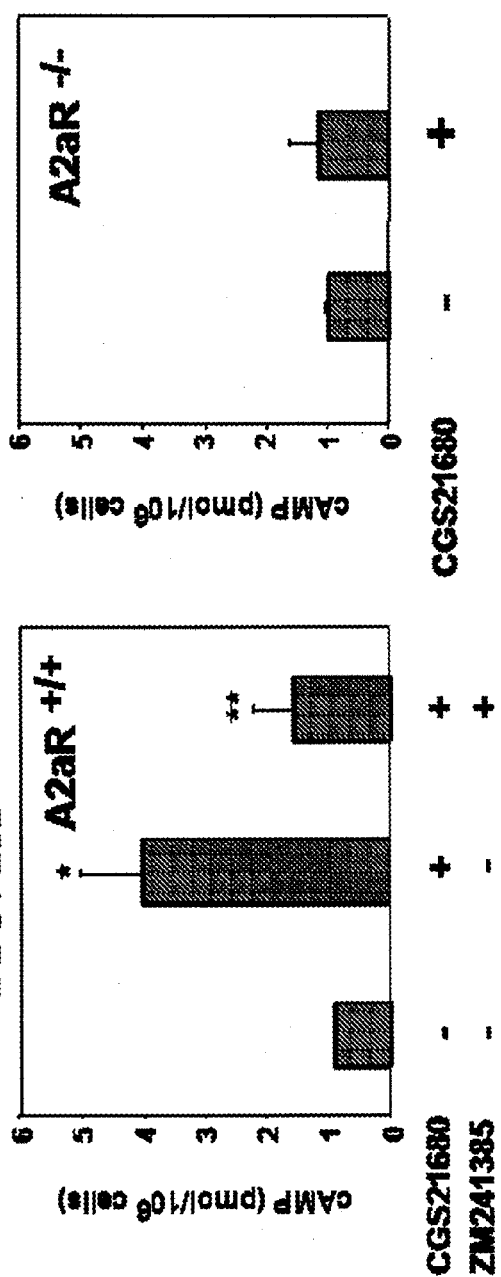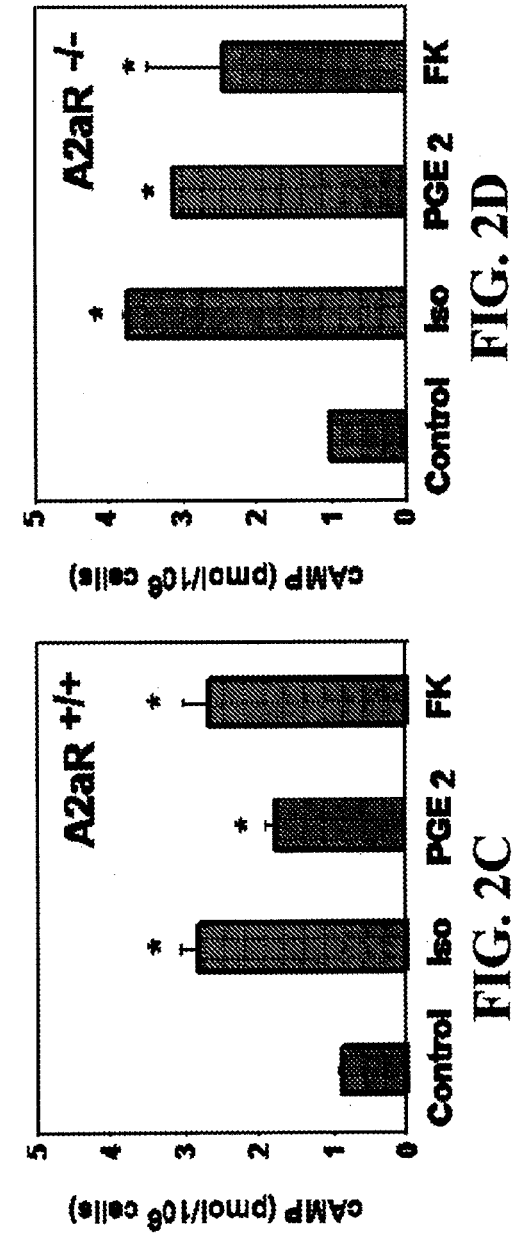

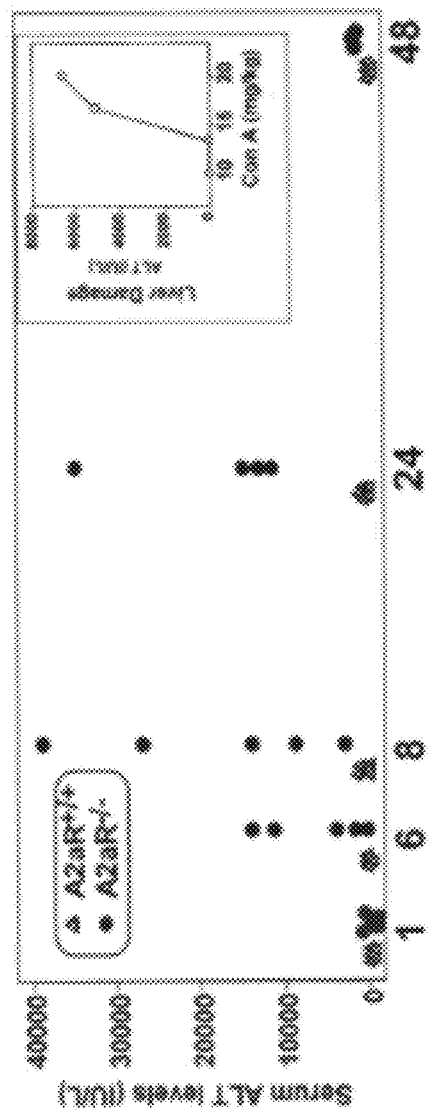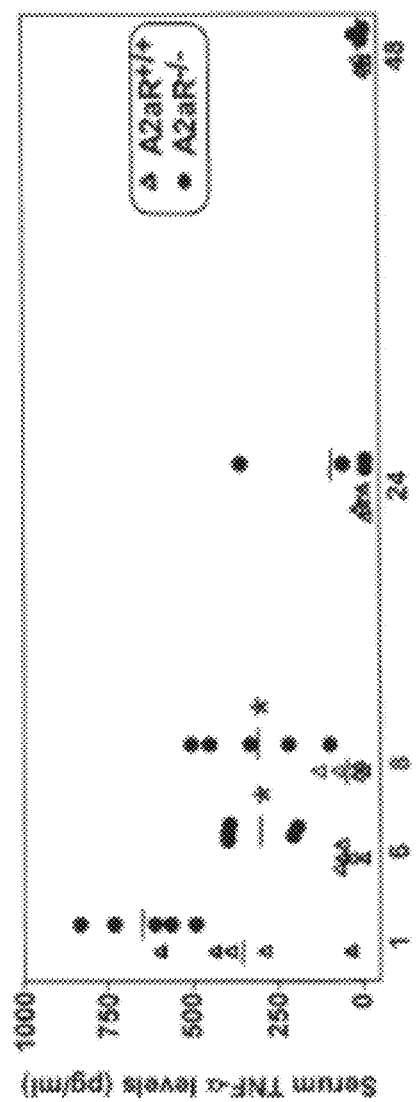
FIG. 3A
FIG. 3B

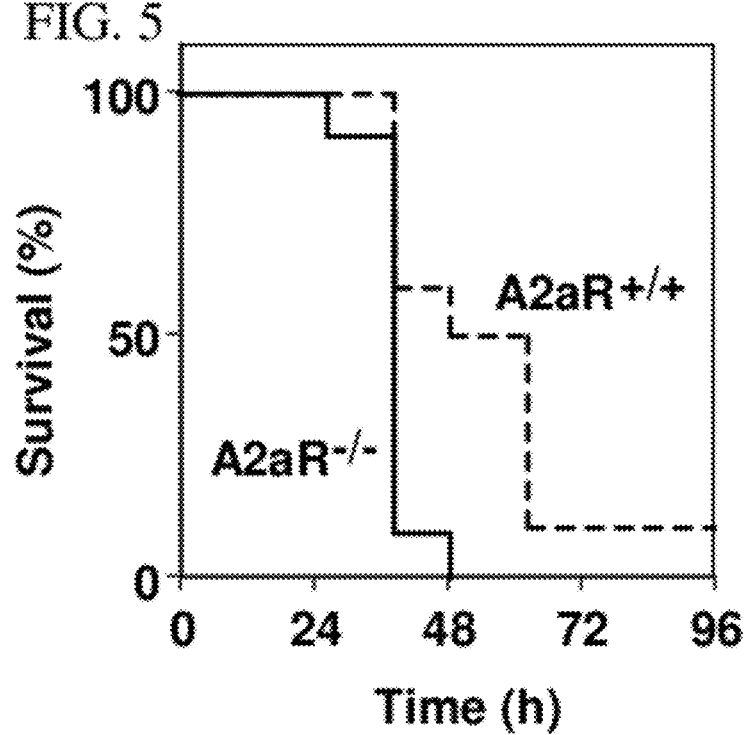

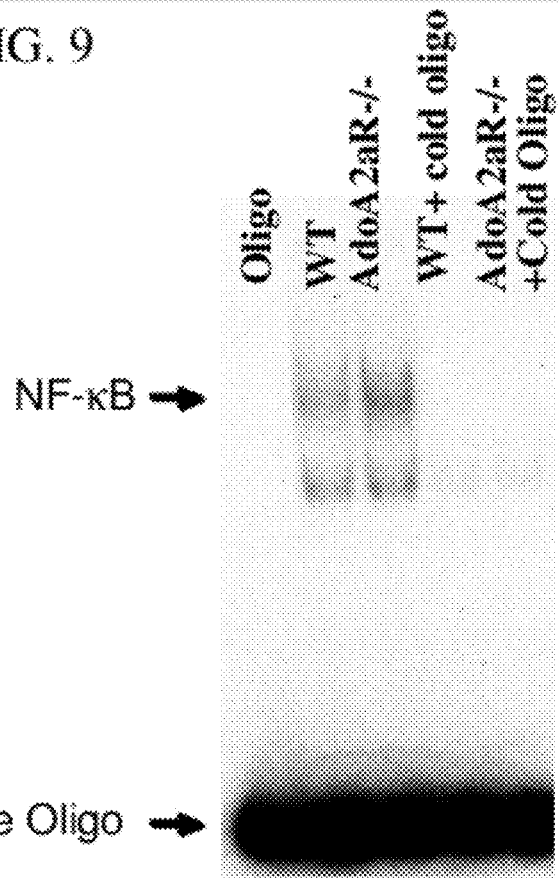
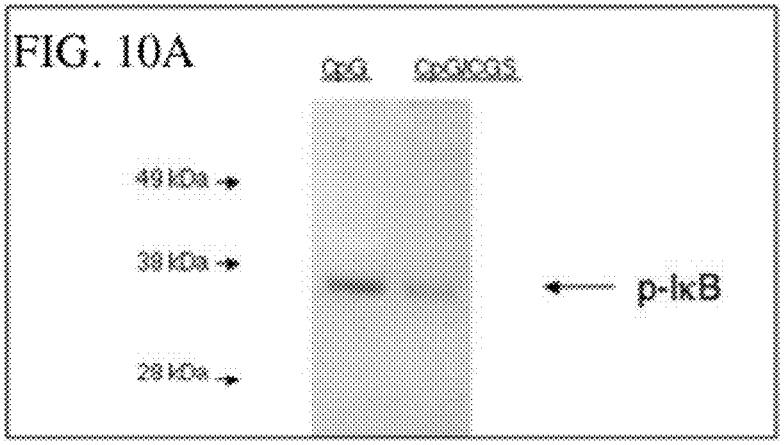
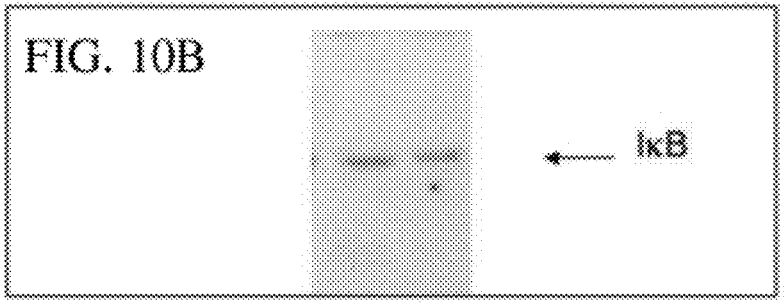

METHODS FOR USING EXTRACELLULAR ADENOSINE INHIBITORS AND ADENOSINE RECEPTOR INHIBITORS TO ENHANCE IMMUNE RESPONSE AND INFLAMMATION

CROSS REFERENCE TO RELATED APPLICATIONS

This application is a divisional of U.S. application Ser. No. 10/498,416 filed Jun. 10, 2004, U.S. Pat. No. 8,080,554, which is the U.S. National Stage of International Application No. PCT/US02/36829 filed Nov. 14, 2002, which claims priority to U.S. Provisional Application Nos. 60/340,772 filed Dec. 12, 2001 and 60/342,585 filed Dec. 19, 2001, all hereby incorporated by reference in their entirety.

FIELD

This application relates to the use of inhibitors of extracellular adenosine and/or inhibitors of adenosine receptors, such as adenosine receptor antagonists and agents that decrease formation or degrade extracellular adenosine, to enhance an immune response and inflammation, and in some examples modulate NF-kB activity.

BACKGROUND

The inflammatory response helps eliminate harmful agents from the body, but inflammation is also a non-specific response that can harm healthy tissue. There is a wide range of pathogenic insults that can initiate an inflammatory response including infection, allergens, autoimmune stimuli, immune response to transplanted tissue, noxious chemicals, and toxins, ischemia/reperfusion, hypoxia, mechanical and thermal trauma, as well as growth of tumors. Inflammation is normally a localized action that results in expulsion or dilution of a pathogenic agent, resulting in isolation of the damaging agent and injured tissue. The cells involved in inflammation include leukocytes (i.e. the immune system cells—neutrophils, eosinophils, lymphocytes, monocytes, basophils, macrophages, B cells, dendritic cells, granulocytes and mast cells), the vascular endothelium, vascular smooth muscle cells, fibroblasts, and myocytes.

Adenosine modulates diverse physiological functions including induction of sedation, vasodilatation, suppression of cardiac rate and contractility, inhibition of platelet aggregability, stimulation of gluconeogenesis and inhibition of lipolysis (see, Stiles, *Trends Pharmacol. Sci.* 7:486, 1986; Williams, *Ann. Rev. Pharmacol. Toxicol.* 27:315, 1987; Ramkumar et al., *Prog. Drug. Res.* 32:195, 1988). In addition, adenosine and some adenosine analogs that non-selectively activate adenosine receptor subtypes decrease neutrophil production of inflammatory oxidative products (Cronstein et al., *Ann. N.Y. Acad. Sci.* 451:291, 1985; Roberts et al., *Biochem. J.,* 227:669, 1985; Schrier et al., *J. Immunol.* 137:3284, 1986; Cronstein et al., *Clinical Immunol. Immunopath.* 42:76, 1987).

Based on biochemical and pharmacological criteria, four subtypes of adenosine receptors have been differentiated: A2a, A2b, A1, and A3. A1 and A3 inhibit, and A2a and A2b stimulate, adenylate cyclase, respectively (Stiles, ibid; Williams, ibid; see also U.S. Pat. No. 5,441,883 for A3 receptors). Substantial progress has been made concerning the biochemical and pharmacological properties of these adenosine receptors such as ligand binding characteristics, glycosylation, and regulation. In addition to its effects on adenylate cyclase, adenosine opens potassium channels, reduces flux through calcium channels, and inhibits or stimulates phosphoinositide turnover through receptor-mediated mechanisms (Fredholm and Dunwiddie, *Trends Pharmacol. Sci.* 9:130, 1988; Sebastiao et al., *Br. J. Pharmacol.* 100:55, 1990; Stiles, *Clin. Res.* 38:10, 1990; and Nakahata et al., *J. Neurochem.* 57:963, 1991). The cDNAs that encode the A1, A2, and A3 adenosine receptors have been cloned (Libert et al., *Science* 244:569, 1989; Maenhaet et al., *Biochem. Biophys. Res. Commun.* 173:1169, 1990; Libert et al., *EMBO J.* 10:1677, 1991; Mahan et al., *Molecular Pharmacol.* 40:1, 1991; Reppert et al., *Molec. Endo.* 5:1037-1048, 1991; U.S. Pat. No. 5,441,883). Molecular cloning of the adenosine receptors has revealed that they belong to the superfamily of G-protein coupled receptors.

SUMMARY

It is disclosed herein that adenosine receptors play a non-redundant role in down-regulation of inflammation in vivo by acting as a physiological "STOP" (a termination mechanism) that can limit the immune response and thereby protect normal tissues form excessive immune damage during pathogenesis of different diseases. Adenosine receptors, such as A2a, A2b, and A3, are shown to down-regulate the immune response during inflammation and protect tissues from immune damage. Inhibition of signaling through the adenosine receptor can be used to intensify and prolong the immune response.

Methods are provided herein to increase an immune response. In one example, the method increases desirable and targeted tissue damage, such as damage of a tumor, for example cancer. Disclosed herein are methods of inhibiting one or more processes conducive to the production of extracellular adenosine and adenosine-triggered signaling through adenosine receptors. For example, enhancement of an immune response, local tissue inflammation, and targeted tissue destruction is accomplished by: inhibiting or reducing the adenosine-producing local tissue hypoxia; by degrading (or rendering inactive) accumulated extracellular adenosine; by preventing or decreasing expression of adenosine receptors on immune cells; and/or by inhibiting/antagonizing signaling by adenosine ligands through adenosine receptors. The results disclosed herein demonstrate that by in vivo administration of agents that disrupt the "hypoxia→adenosine accumulation→immunosuppressive adenosine receptor signaling to immune cells" pathway in subjects suffering from various diseases (e.g. cancer and sepsis) can result in in vivo treatment of tumors or improved immunization.

In one example, the method includes administering one or more inhibitors of extracellular adenosine and/or adenosine receptor inhibitors, such as an adenosine receptor antagonist. To increase the efficacy of a vaccine, one or more adenosine receptor inhibitors and/or inhibitors of extracellular adenosine can be administered in conjunction with the vaccine. In one example, one or more adenosine receptor inhibitors or inhibitors of extracellular adenosine are administered to increase an immune response/inflammation. In another example, a method is provided to achieve targeted tissue damage, such as for tumor destruction.

BRIEF DESCRIPTION OF THE FIGURES

FIGS. 2A and 2B are bar graphs showing cAMP levels in lymphoid cells from (A) wild-type (A2aR+/+) or (B) A2aR deficient (A2aR$^{-/-}$) mice treated with CGS21680 alone, or CGS21680 and ZM241385.

FIGS. 2C and 2D are bar graphs showing cAMP levels in lymphoid cells in (C) wild-type (A2aR+/+) or (D) A2aR deficient (A2aR$^{-/-}$) treated with FK, isoproterenol, or PGE$_2$. The differences between treated and untreated mice are statistically significant as indicated by the asterisk (*P<0.05).

FIGS. 3A and 3B are dot plots showing serum levels of (A) ALT or (B) TNF-α in A2aR$^{+/+}$ and A2aR$^{-/-}$ mice at various time points.

FIG. 5 is a survival graph showing that A2a receptors protect against death from septic shock. *P<0.05.

FIG. 9 is a digital image showing the results of a nuclear extract electrophoretic mobility shift assay of macrophages that demonstrates that A2a receptors negatively regulate NF-kB translocation into the nucleus, and thereby its activity, in vivo.

FIGS. 10 A and 10B are digital images of Western blots showing that adenosine receptors negatively regulate NF-kB translocation by inhibiting phosphorylation of Ik-B by IKK kinase.

SEQUENCE LISTING

Figure 1A:
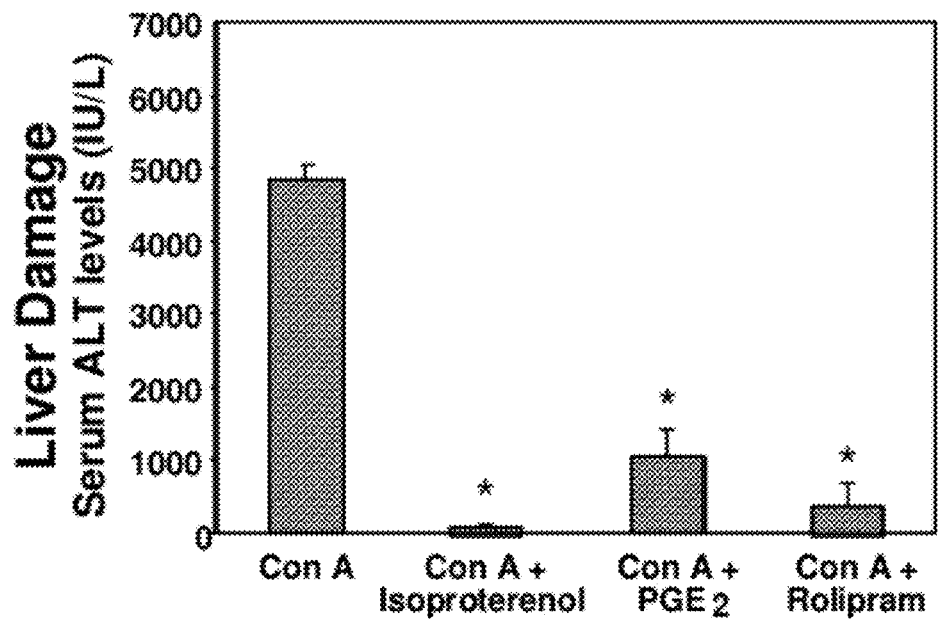
FIG. 1A is a bar graph showing that pharmacologically activated cAMP-elevating receptors or increases in cAMP are capable of blocking inflammation in vivo. The differences between treated and untreated mice are statistically significant as indicated by the asterisk (*$P<0.05$).

The nucleic acid sequence listed in the accompanying sequence listing are shown using standard letter abbreviations for nucleotide bases. Only one strand of each nucleic acid sequence is shown, but the complementary strand is understood as included by any reference to the displayed strand.

SEQ ID NO: 1 shows the nucleotide sequence of a CpG oligonucleotide.

DETAILED DESCRIPTION OF SEVERAL SPECIFIC EMBODIMENTS

Abbreviations

Adora1 Adenosine receptor A1
Adora2a Adenosine receptor A2a
Adora2b Adenosine receptor A2b
Adora3 Adenosine receptor A3
ADA Adenosine deaminase, adenosine degrading enzyme
ADA-PEG Polyethylene glycol-modified ADA to extend half life in vivo
ADA SCID Adenosine deaminase severe combined immunodeficiency
ALT Alanine aminotransferase. Liver enzyme
cAMP Cyclic adenosine monophosphate
CGS CGS21680
Con A: Concanavalin A
FK Forskolin
H-E Haematoxylin and eosin
IL-12p40 Interleukin-12p40
IL-1β Interleukin-1β
IL-6 Interleukin-6
Iso Isoproterenol
LPS Lipopolysaccharide, bacterial endotoxin
PEA *Pseudomonas* exotoxin A
PGE$_2$ Prostaglandin E2
TNF-α Tumor necrosis factor α

Terms

The following explanations of terms and methods are provided to better describe the present disclosure and to guide those of ordinary skill in the art in the practice of the present disclosure. As used herein and in the claims, the singular forms "a" or "an" or "the" include plural references unless the context clearly dictates otherwise. For example, reference to "an adenosine receptor antagonist" includes a plurality of such antagonists and reference to "the adenosine receptor" includes reference to one or more receptors and equivalents thereof known to those skilled in the art, and so forth. Similarly, the word "or" is intended to include "and" unless the context clearly indicates otherwise.

Unless explained otherwise, all technical and scientific terms used herein have the same meaning as commonly understood to one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biol-*

*ogy and Biotechnology: a Comprehensive Desk Reference*, published by VCH Publishers, Inc., 1995 (ISBN 1-56081-569-8). Although methods and materials similar or equivalent to those described herein can be used in the practice or testing of the present disclosure, suitable methods and materials are described below. The materials, methods, and examples are illustrative only and not intended to be limiting.

Adenosine: A ribonucleotide which includes the nitrogenous base, adenine, linked to the sugar, ribose.

Adenosine receptors: At least four subtypes of adenosine receptor (Adora1, Adora2a, Adora2b, and Adora3, also called A1, A2a, A2b, and A3, respectively) have been cloned. Adenosine receptors include both naturally occurring peptides, as well as adenosine receptor fragments and variants that retain full or partial adenosine receptor biological activity. Adenosine receptors are members of the G-protein coupled receptor (GPCR) superfamily, and are thought to mediate stimulation or inhibition of adenylyl cyclase activity, and hence cyclic AMP levels. The effects on cAMP levels of the methylxanthine antagonists of adenosine receptors (such as caffeine, and theophylline which are present in tea, coffee and cocoa) are known.

The A1 receptor is linked to inhibition of adenylyl cyclase activity. However, there is also evidence for coupling (via G-proteins) to ion channels, and phospholipase C. In the nervous system, the A1 adenosine receptor mediates inhibition of transmitter release and the reduction in neuronal activity. Blockade of this receptor in the heart leads to the accelerated, pronounced "pounding" observed after drinking large amounts of strong coffee (due to caffeine and theophylline). In one example, A1 is shown as GenBank Accession No. L22214.

A2a is almost exclusively coupled to stimulation of adenylyl cyclase activity. Its distribution in the CNS is very discrete, being heavily localized in the caudate and putamen bodies, and the nucleus accumbens and olfactory tubercle. In the periphery, the A2a receptor is present on platelets and is anti-aggregatory. In one embodiment, A2A is shown as GenBank Accession No. AH003248, and A2b is shown as GenBank Accession No. NM000676. A2a and A2b receptors cause similar cellular effects, but have different tissue distribution and requirements for the levels of extracellular adenosine needed for their activation. It appears that A2b receptor is activated by higher levels of adenosine then A2a receptor (Linden, *Ann. Rev Pharmacol. Toxicol.* 41:775-87, 2001).

A3 couples to inhibition of adenylyl cyclase activity. In one example, A3 is shown as GenBank Accession No. AH003597.

Adenosine receptor inhibitor: Any agent or composition that decreases the activity of an adenosine receptor. For example, such an inhibitor may decrease the activity of an adenosine receptor, as compared to the activity of the adenosine receptor in the absence of such an inhibitor. Examples include, but are not limited to, a pharmacological antagonist, a gene therapy agent, a ribozyme, an antisense oligonucleotide, or another catalytic nucleic acid that selectively binds mRNA encoding an adenosine receptor.

Adjuvant: Any agent that enhances or increases one or more immune-stimulating properties of another agent (such as a chemical compound or antigenic epitope). An adjuvant augments, stimulates, activates, potentiates, or modulates the immune response at the cellular or humoral level.

For example, addition of an adjuvant to a vaccine improves the immune response of a cell, such as a cell in a subject. An adjuvant can be used so that less vaccine is needed to produce the immune response. One specific, non-limiting example of an adjuvant is Freund's adjuvant, which is a water-in-oil emulsion that contains an immunogen, an emulsifying agent and mycobacteria. The classical agents (Freund's adjuvant, BCG, *Corynebacterium parvum*) contain bacterial antigens. Some adjuvants are endogenous (e.g. histamine, interferon, transfer factor, tuftsin, interleukin-1 and interleukin-12). The mode of action of an adjuvant can be non-specific, resulting in increased immune responsiveness to a wide variety of antigens, or antigen-specific, i.e. affecting a restricted type of immune response to a narrow group of antigens. The therapeutic efficacy of many biological response modifiers is related to their antigen-specific immunoadjuvanticity.

Agent: Any polypeptide, compound, small molecule, organic compound, salt, polynucleotide, peptidomimetic, or other molecule of interest.

Agonist: An agent that has affinity for and stimulates physiologic activity of a receptor normally stimulated by one or more naturally occurring agents, thus triggering a biochemical response. In one example, one molecule of agonist (A) binds reversibly to a receptor molecule (R) to form an active agonist-receptor complex (AR), which generates a pharmacological response while the agonist remains bound.

Antagonist: An agent that tends to nullify the action of another, as a drug that binds to a receptor without eliciting a biological response. In one example, an antagonist is a chemical compound that is an antagonist for an adenosine receptor, such as the A2a, A2b, or A3 receptor. Specific examples of adenosine receptor antagonists, include, but are not limited to: ZM241385; 1,7, methylxantine (caffeine); theophylline; theobromine; SCH 58261 [7-(2-phenylethyl)-5-amino-2-(2-furyl)-pyrazolo-[4,3-e]-1,2,4-triazolo[1,5-c]pyrimidine] (Schering-Plough Research Institute, Milan, Italy); and KW-6002 [(E)-1,3-diethyl-8-(3,4-dimethoxystyryl)-7-methyl-3,7-dihydro-1H-purine-2,6-dione] (Kyowa Hakko Kogyo Co. Ltd., Shizuoka, Japan). Particular non-limiting examples of antagonists are described in U.S. Pat. Nos. 5,565,566; 5, 545, 627, 5,981,524; 5,861,405; 6,066,642; 6,326,390; 5,670,501; 6,117,998; 6,232,297; 5,786,360; 5,424,297; 6,313,131, 5,504,090; and 6,322,771. In another example, an adenosine receptor antagonist is an antisense oligonucleotide, ribozyme, or other catalytic nucleic acid that selectively binds mRNA encoding the adenosine receptor.

Animal: Living multi-cellular vertebrate organisms, a category that includes, for example, mammals and birds. The term mammal includes both human and non-human mammals. Similarly, the term "subject" includes both human and veterinary subjects.

Antibody: Immunoglobulin molecules and immunologically active portions of immunoglobulin molecules, i.e. molecules that contain an antigen-binding site that specifically binds (immunoreacts with) an antigen. A naturally occurring antibody (e.g. IgG) includes four polypeptide chains, two heavy (H) chains and two light (L) chains inter-connected by disulfide bonds. However, the antigen-binding function of an antibody can be performed by fragments of a naturally-occurring antibody. Thus, these antigen-binding fragments are also designated by the term "antibody".

Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., *Nature* 341:544-6, 1989) which consists of a VH domain; (v) an isolated complimentarity determining region (CDR); and (vi) an F(ab')$_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. *Science* 242:423-6, 1988; and Huston et al. *Proc. Natl. Acad. Sci.* 85:5879-83, 1988) by recombinant methods. Such single chain antibodies are also included.

In one example, antibody fragments are those which are capable of crosslinking their target antigen, e.g., bivalent fragments such as F(ab')$_2$ fragments. Alternatively, an antibody fragment which does not itself crosslink its target antigen (e.g., a Fab fragment) can be used in conjunction with a secondary antibody which serves to crosslink the antibody fragment, thereby crosslinking the target antigen. Antibodies can be fragmented using conventional techniques and the fragments screened for utility in the same manner as described for whole antibodies. An antibody is further intended to include bispecific and chimeric molecules that specifically bind the target antigen.

"Specifically binds" refers to the ability of individual antibodies to specifically immunoreact with an antigen, such as a T cell surface molecule. The binding is a non-random binding reaction between an antibody molecule and an antigenic determinant of the T cell surface molecule. The desired binding specificity is typically determined from the reference point of the ability of the antibody to differentially bind the T cell surface molecule and an unrelated antigen, and therefore distinguish between two different antigens, particularly where the two antigens have unique epitopes. An antibody that specifically binds to a particular epitope is referred to as a "specific antibody."

Antigen: A compound, composition, or agent capable of being the target of inducing a specific immune response, such as stimulate the production of antibodies or a T-cell response in a subject, including compositions that are injected or absorbed into a subject. An antigen reacts with the products of specific humoral or cellular immunity, including those induced by heterologous immunogens. The term "antigen" includes all related antigenic epitopes.

Antisense, Sense, and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T). Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Antisense oligonucleotide: A sequence of at least about 8 nucleotides, such as about at least 10, 12, 15, 20, 30 or 50 nucleotides, wherein the sequence is from a gene sequence (such as all or a portion of a cDNA or gene sequence, or the reverse complement thereof), arranged in reverse orientation relative to the promoter sequence in a transformation vector.

In one example, the sequence is an adenosine receptor sequence (e.g. Genbank accession number L22214, AH003248, NM000676, and AH003597). Where the reverse complement of a adenosine receptor sequence is used to suppress expression of proteins from the adenosine receptor locus, the sense strand of adenosine or adenosine receptor locus or cDNA is inserted into the antisense construct. A reduction of adenosine receptor protein expression in a transgenic cell can be obtained by introducing into cells an antisense oligonucleotide based on an adenosine receptor locus, e.g. the adenosine receptor A1, A2a, A2b, or A3 locus, including the reverse complement of the adenosine receptor cDNA coding sequence, the adenosine receptor cDNA or gene sequence or flanking regions thereof.

The introduced sequence need not be the full-length human adenosine receptor cDNA or gene or reverse complement thereof, and need not be exactly homologous to the equivalent sequence found in the cell type to be transformed. Generally, however, where the introduced sequence is of shorter length, a higher degree of homology to the native adenosine or adenosine receptor locus sequence will be needed for effective antisense suppression. The introduced antisense sequence in the vector can be at least 30 nucleotides in length, and improved antisense suppression will typically be observed as the length of the antisense sequence increases, such as when the sequence is greater than 100 nucleotides. For suppression of the adenosine receptor gene itself, transcription of an antisense construct results in the production of RNA molecules that are the reverse complement of mRNA molecules transcribed from the endogenous adenosine receptor gene in the cell. For suppression of protein expression from the opposite strand of the adenosine receptor locus, transcription of an antisense construct results in the production of RNA molecules that are identical to the mRNA molecules transcribed from the endogenous adenosine or adenosine receptor gene, assuming the antisense construct was generated from sequence within the adenosine receptor gene rather than in a flanking region. Antisense molecules made to target the sequence that is the reverse complement of the adenosine receptor locus will serve to suppress any abnormal expression of proteins or peptides from the strand of the locus not encoding the adenosine receptor cDNA.

Autoimmune disorder: A disorder in which the immune system produces an immune response (e.g. a B cell or a T cell response) against an endogenous antigen, with consequent injury to tissues.

Avidity: The overall strength of interaction between two agents or molecules, such as an antigen and an antibody. Avidity depends on both the affinity and the valency of interactions. Therefore, the avidity of a pentameric IgM antibody, with ten antigen binding sites, for a multivalent antigen can be much greater than the avidity of a dimeric IgG molecule for the same antigen.

B cell or B lymphocyte: One of the two major types of lymphocyte. The antigen receptor on B lymphocytes, sometimes called the B cell receptor, is a cell-surface immunoglobulin. On activation by an antigen, B cells differentiate into cells producing antibody molecules of the same antigen-specificity as this receptor.

Binding or stable binding: An oligonucleotide binds or stably binds to a target nucleic acid if a sufficient amount of the oligonucleotide forms base pairs or is hybridized to its target nucleic acid to permit detection of that binding. Binding can be detected by either physical or functional properties of the target:oligonucleotide complex. Binding between a target and an oligonucleotide can be detected by any procedure known to one skilled in the art, including both functional and physical binding assays. Binding can be detected functionally by determining whether binding has an observable effect upon a biosynthetic process such as expression of a gene, DNA replication, transcription, translation and the like.

Physical methods of detecting the binding of complementary strands of DNA or RNA include such methods as DNase I or chemical footprinting, gel shift and affinity cleavage assays, Northern blotting, dot blotting and light absorption detection procedures. For example, one method that is widely used involves observing a change in the light absorption of a solution containing an oligonucleotide (or an analog) and a target nucleic acid at 220 to 300 nm as the temperature is slowly increased. If the oligonucleotide or analog has bound to its target, there is an increase in absorption at a characteristic temperature as the oligonucleotide (or analog) and target disassociate from each other, or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Biological samples: Suitable biological samples include samples containing genomic DNA, RNA (including mRNA), and/or protein, obtained from cells of a subject. Examples include, but are not limited to, peripheral blood, urine, semen, saliva, tissue biopsy, surgical specimen, amniocentesis samples, derivatives and fractions of blood such as serum, and biopsy material.

Cancer: Malignant neoplasm that has undergone characteristic anaplasia with loss of differentiation, increase rate of growth, invasion of surrounding tissue, and is capable of metastasis.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Complementarity and percentage complementarity: Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide remains detectably bound to a target nucleic acid sequence under the required conditions.

Complementarity is the degree to which bases in one nucleic acid strand base pair with the bases in a second nucleic acid strand. Complementarity is conveniently described by percentage, i.e. the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

In the present disclosure, "sufficient complementarity" means that a sufficient number of base pairs exist between the oligonucleotide and the target sequence to achieve detectable binding, and in the case of the binding of an antigen, disrupt expression of gene products (such as adenosine receptors). When expressed or measured by percentage of base pairs formed, the percentage complementarity that fulfills this goal can range from as little as about 50% complementarity to full, (100%) complementary. In general, sufficient complementarity is at least about 50%, for example at least 75%, 90%, 95%, 98% or even 100% complementarity.

A thorough treatment of the qualitative and quantitative considerations involved in establishing binding conditions that allow one skilled in the art to design appropriate oligonucleotides for use under the desired conditions is provided by Beltz et al. *Methods Enzymol* 100:266-285, 1983, and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

Comprises: A term that means "including." For example, "comprising A or B" means including A or B, or both A and B, unless clearly indicated otherwise.

Cytokine: Proteins made by cells that affect the behavior of other cells, such as lymphocytes. In one example, a cytokine is a chemokine, a molecule that affects cellular trafficking.

DNA: Deoxyribonucleic acid. DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Deletion: The removal of a sequence of DNA, the regions on either side being joined together.

Differentiation: The process by which cells become more specialized to perform biological functions. Differentiation is a property that is totally or partially lost by cells that have undergone malignant transformation.

Epitope: An antigenic determinant. These are particular chemical groups or peptide sequences on a molecule that are antigenic, i.e. that elicit a specific immune response. An antibody binds a particular antigenic epitope.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence. For example, a therapeutically effective oligonucleotide can be complementary to an adenosine receptor-encoding mRNA, or an adenosine receptor-encoding dsDNA.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11.

For the purpose of the present disclosure, "stringent conditions" encompass conditions under which hybridization will only occur if there is less than 25% mismatch between the hybridization molecule and the target sequence. "Stringent conditions" can be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

Hypersensitivity: Immune responses to innocuous antigens that lead to symptomatic reactions upon re-exposure are called hypersensitivity reactions. These can cause hypersensitivity diseases if they occur repetitively. This state of heightened reactivity to an antigen is called hypersensitivity. Hypersensitivity reactions are classified by mechanism: type I hypersensitivity reactions involve IgE antibody triggering of mast cells; type II hypersensitivity reactions involve IgG antibodies against cell-surface or matrix antigens; type III hypersensitivity reactions involve antigen:antibody complexes; and type iV hypersensitivity reactions are T cell-mediated.

Immune cell: Any cell involved in a host defense mechanism, such as cells that produces pro-inflammatory cytokines, and such as cells that participate in tissue damage and/or disease pathogenesis. Examples include, but are not limited to: T cells, B cells, natural killer cells, neutrophils, mast cells, macrophages, antigen-presenting cells, basophils, and eosinophils.

Immune response: A change in immunity, for example, a response of a cell of the immune system, such as a B cell or T cell, to a stimulus. In one example, the response is specific for a particular antigen (an "antigen-specific response"). In one example, an immune response is a T cell response, such as a Th1, Th2, or Th3 response. In a particular example, an increased or enhanced immune response is an increase in the ability of a subject to fight off a disease, such as a viral infection or tumor.

Immunoglobulins: A class of proteins found in plasma and other body fluids that exhibits antibody activity and binds with other molecules with a high degree of specificity; divided into five classes (IgM, IgG, IgA, IgD, and IgE) on the basis of structure and biological activity. Immunoglobulins and certain variants thereof are known and many have been prepared in recombinant cell culture (e.g. see U.S. Pat. No. 4,745,055; U.S. Pat. No. 4,444,487; WO 88/03565; EP 256, 654; EP 120,694; EP 125, 023; Faoulkner et al., *Nature* 298: 286, 1982; Morrison, *J. Immunol.* 123:793, 1979; Morrison et al., *Ann Rev. Immunol* 2:239, 1984).

A native (naturally occurring) immunoglobulin is made up of four polypeptide chains. There are two long chains, called the "heavy" or "H" chains which weigh between 50 and 75 kilodaltons and two short chains called "light" or "L" chains weighing in at 25 kilodaltons. They are linked together by disulfide bonds to form a "Y" shaped molecule. Each heavy chain and light chain can be divided into a variable region and a constant region. An Fc region includes the constant regions of the heavy and the light chains, but not the variable regions.

Inhibitor of extracellular adenosine: Any agent or composition that decreases the activity or level of extracellular adenosine. Examples include, but are not limited to, agents that degrade extracellular adenosine, render extracellular adenosine inactive, and/or decrease or prevent the accumulation or formation of extracellular adenosine. Particular examples include, but are not limited to, enzymes such as adenosine deaminase, adenosine kinase, and adenosine kinase enhancers; oxygenation; redox-potential changing agents which diminish the degree of hypoxia-ischemia; and other catalytic agents that selectively bind and decrease or abolish the ability of endogenously formed adenosine to signal through adenosine receptors. Other examples include cell culture conditions that result in negative selection of cells with adenosine receptors and enrichment of cell populations without adenosine receptors.

Inflammation: When damage to tissue occurs, the body's response to the damage is usually inflammation. The damage can be due to trauma, lack of blood supply, hemorrhage, autoimmune attack, transplanted exogenous tissue, or infection. This generalized response by the body includes the release of many components of the immune system (e.g. IL-1 and TNF), attraction of cells to the site of the damage, swelling of tissue due to the release of fluid and other processes.

Inflammation, the response of tissue to injury, is divided into two phases, termed acute and chronic. In the acute phase, inflammation is characterized by increased blood flow and vascular permeability, accumulation of fluid, and accumulation of leukocytes and inflammatory mediators (e.g. cytokines). In the subacute/chronic phase, inflammation is characterized by the development of specific humoral and cellular immune responses to the pathogen(s) present at the site of tissue injury. During both the acute and chronic inflammatory processes, a variety of soluble factors are involved in leukocyte recruitment through increased expression of cellular adhesion molecules and chemoattraction. Many of these soluble mediators regulate the activation of both the resident cells (such as fibroblasts, endothelial cells, tissue macrophages, and mast cells) and newly recruited inflammatory cells (such as monocytes, lymphocytes, neutrophils, and eosinophils).

Isolated: An "isolated" biological component (such as a nucleic acid or protein) has been substantially separated, produced apart from, or purified away from other biological components in the cell of the organism in which the component naturally occurs, i.e. other chromosomal and extrachromosomal DNA and RNA, and proteins. Nucleic acids and proteins that have been "isolated" thus include nucleic acids and proteins purified by standard purification methods. The term also embraces nucleic acids and proteins prepared by recombinant expression in a host cell as well as chemically synthesized nucleic acids.

Leukocyte: Cells in the blood, also termed "white cells," that are involved in defending the body against infective organisms and foreign substances. Leukocytes are produced in the bone marrow. There are 5 main types of white blood cells, subdivided between 2 main groups: polymorphonuclear leukocytes (neutrophils, eosinophils, basophils) and mononuclear leukocytes (monocytes and lymphocytes). When an infection is present, the production of leukocytes increases.

Lymphocytes: A type of white blood cell that is involved in the immune defenses of the body. There are two main types of lymphocytes: B-cells and T-cells.

Mammal: This term includes both human and non-human mammals. Similarly, the term "subject" includes both human and veterinary subjects.

Monoclonal antibody: An antibody produced by a single clone of B-lymphocytes. Monoclonal antibodies are produced by methods known to those of skill in the art, for instance by making hybrid antibody-forming cells from a fusion of myeloma cells with immune spleen cells.

Natural killer (NK) cell: These are large, usually granular, non-T, non-B lymphocytes, which kill certain tumor cells. NK cells are important in innate immunity to viruses and other intracellular pathogens, as well as in antibody-dependent cell-mediated cytotoxicity (ADCC).

Neoplasm: An abnormal mass of tissue that results from excessive cell division that is uncontrolled and progressive, also called a tumor. Neoplasms can be begin (neither infiltrative nor cancerous) or malignant (invasive).

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear polynucleotide sequence of up to about 200 nucleotide bases in length, for example a polynucleotide (such as DNA or RNA) which is at least 6 nucleotides, for example at least 15, 25, 50, 75, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Pharmaceutical agent: A chemical compound or composition capable of inducing a desired therapeutic or prophylactic effect when properly administered to a subject or a cell. "Incubating" includes a sufficient amount of time for an agent to interact with a cell. "Contacting" includes incubating an agent in solid or in liquid form with a cell.

Pharmaceutically acceptable carriers: The pharmaceutically acceptable carriers useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of adenosine receptor inhibitors and/or inhibitors of extracellular adenosine.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A linear nucleotide sequence, including sequences of greater than 100 nucleotide bases in length.

Polypeptide: Any chain of amino acids, regardless of length or post-translational modification (e.g. glycosylation or phosphorylation).

Preventing or treating a disease: "Preventing" a disease refers to inhibiting or decreasing the full development of a disease, for example in a person who is known to have a predisposition to a disease. An example of a person with a known predisposition is someone with a history of diabetes in the family, or who has been exposed to factors that predispose the subject to a condition, such as lupus or rheumatoid arthritis. "Treatment" refers to a therapeutic intervention that ameliorates a sign or symptom of a disease or pathological condition after it has begun to develop.

Probes and primers: Nucleic acid probes and primers can be readily prepared based on a nucleic acid sequence. A probe includes an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g. in Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992).

Primers are short nucleic acid molecules, such as DNA oligonucleotides at least 10 nucleotides in length, such as about at least 12, 15, 17, 20, or 25 nucleotides in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g. by the polymerase chain reaction (PCR) or other nucleic-acid amplification methods known in the art.

Methods for preparing and using probes and primers are described, for example, in Sambrook et al. (In *Molecular Cloning: A Laboratory Manual*, CSHL, New York, 1989), Ausubel et al. (In *Current Protocols in Molecular Biology*, Greene Publ. Assoc. and Wiley-Intersciences, 1998), and Innis et al. (PCR *Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer of 30 consecutive nucleotides of a adenosine receptor encoding nucleotide will anneal to a target sequence, such as another nucleic acid encoding an adenosine receptor, with a higher specificity than a corresponding primer of only 15 nucleotides. Thus, in order to obtain greater specificity, probes and primers can be selected that include at least 17, 20, 23, 25, 30, 35, 40, 45, 50 or more consecutive nucleotides of nucleotide sequence of interest.

Purified: The term purified does not require absolute purity; rather, it is intended as a relative term. Thus, for example, a purified peptide or nucleic acid preparation is one in which the peptide or nucleic acid is more enriched than the peptide or nucleic acid is in its natural environment within a cell. For example, a preparation is purified such that the protein or nucleic acid represents at least 50%, such as at least 70%, of the total peptide or nucleic acid content of the preparation.

Receptor: A molecular structure within a cell or on the surface of a cell, characterized by selective binding of a specific substance and a specific physiological effect that accompanies the binding, for example, cell surface receptors for peptide hormones, neurotransmitters, immunoglobulins, small molecules, and cytoplasmic receptors for steroid hormones. An adenosine receptor is a cell surface receptor for adenosine, and includes, but is not limited to, A2 and A3 receptors.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g. by genetic engineering techniques. Similarly, a recombinant protein is one encoded for by a recombinant nucleic acid molecule.

Ribozyme: Synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs can be used to confer RNA cleaving activity on the antisense RNA, such that endogenous mRNA molecules that bind to the antisense RNA are cleaved, which in turn leads to an enhanced antisense inhibition of endogenous gene expression.

Specific binding agent: An agent that binds substantially only to a defined target. Thus an antibody or antibody fragment-specific binding agent binds substantially only the defined antibody or antibody fragment, or an antibody region within a protein, such as a fusion protein. As used herein, the term "adenosine receptor specific binding agent," includes anti-adenosine receptor antibodies (and functional antibody fragments thereof) and other agents (such as potential therapeutic agents) that bind substantially only to adenosine receptors.

Antibodies can be produced using standard molecular procedures described in a number of texts, including Harlow and Lane (*Antibodies, A Laboratory Manual*, CSHL, New York, 1988). The determination that a particular agent binds substantially only to the target protein or peptide can readily be made by using or adapting routine procedures. One suitable in vitro assay makes use of the Western blotting procedure (Harlow and Lane, *Antibodies, A Laboratory Manual*, CSHL, New York, 1988).

Shorter fragments of antibodies can also serve as specific binding agents. For instance, FAbs, Fvs, and single-chain Fvs (SCFvs) that bind to adenosine receptor are adenosine receptor-specific binding agents.

Subject: Living multi-cellular vertebrate organisms, a category that includes both human and non-human mammals.

T Cell: A white blood cell involved in the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8 T cell is a cytotoxic T lymphocyte. In another example, a CD8 cell is a suppressor T cell.

Target sequence: A portion of ssDNA, dsDNA or RNA that, upon hybridization to a therapeutically effective oligonucleotide or oligonucleotide analog, results in the inhibition of gene expression, such as adenosine receptor gene expression. An antisense or a sense molecule can be used to target a portion of dsDNA, since both will interfere with the expression of that portion of the dsDNA. The antisense molecule can bind to the plus strand, and the sense molecule can bind to the minus strand. Thus, target sequences can be ssDNA, dsDNA, and RNA.

Therapeutically effective amount: A quantity of an agent or composition sufficient to achieve a desired effect in a subject being treated. For instance, this can be the amount necessary to increase activity of an immune cell and/or enhance an immune response in a subject. In one example, it is an amount that will inhibit viral, fungal, or bacterial replication or to measurably alter outward symptoms of the viral, fungal, or bacterial infection. In another example, it is an amount that will decrease or prevent further tumor growth. When administered to a subject, a dosage will generally be used that will achieve target tissue concentrations (for example, in lymphocytes) that has been shown to achieve in vitro inhibition of viral replication or reduction of tumor cells.

Therapeutically effective dose: A dose sufficient to prevent advancement, or to cause regression of the disease, for example a dose sufficient to reduce the volume or size of a tumor. In another example, it is an amount which is capable of relieving symptoms caused by a disease, such as pain or swelling.

Therapeutically effective adenosine receptor oligonucleotides and oligonucleotide analogs: Characterized by their ability to inhibit or decrease expression of one or more adenosine receptors. As described below, complete inhibition is not necessary for therapeutic effectiveness. Therapeutically effective oligonucleotides are characterized by their ability to inhibit or decrease the expression of one or more adenosine receptors. Inhibition is a reduction in adenosine receptor expression observed when compared to adenosine receptor production in the absence of the oligonucleotide or oligonucleotide analog. For example, an oligonucleotides may be capable of inhibiting the expression of adenosine receptors by at least 15%, 30%, 40%, 50%, 60%, or 70%, or more, and still be considered to be therapeutically effective.

Therapeutically effective oligonucleotides and oligonucleotide analogs are additionally characterized by being sufficiently complementary to adenosine receptor-encoding nucleic acid sequences. As described herein, sufficient complementary means that the therapeutically effective oligonucleotide or oligonucleotide analog can specifically disrupt the expression of adenosine receptors, and not significantly alter the expression of genes other than adenosine receptors.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Treatment: Refers to both prophylactic inhibition of initial infection, and therapeutic interventions to alter the natural course of an untreated disease process, such as infection with a virus.

Tumor: An abnormal mass of tissue that results from excessive cell division that is uncontrolled and progressive, also called a neoplasm. Tumors can be benign (neither infiltrative nor cancerous) or malignant (invasive).

Vaccine: A dead or attenuated (non-pathogenic) form of a pathogen, or an antigen isolated from a pathogen, administered to a subject to induce adaptive immunity to the pathogen.

Vector: A nucleic acid molecule as introduced into a host cell, thereby producing a transformed host cell. A vector can include nucleic acid sequences that permit it to replicate in the host cell, such as an origin of replication. A vector can also include one or more selectable marker genes and other genetic elements known in the art. The term "vector" includes viral vectors, such as adenoviruses, adeno-associated viruses, vaccinia, and retroviruses vectors.

The Stop Mechanism of Inflammation

It is disclosed herein that the adenosine receptor is a physiological "stop" mechanism for inflammation in vivo, and as such, extracellular adenosine and adenosine receptors (such as A2a, A2b, and A3) are pharmacological and genetic targets for affecting inflammation and thereby altering the immune response. Inhibition or reduction of extracellular adenosine or the adenosine receptor through the use an inhibitor of extracellular adenosine (such as an agent that prevents the formation of, degrades, renders inactive, and/or decreases extracellular adenosine), and/or an adenosine receptor inhibitor (such as an adenosine receptor antagonist), as disclosed herein, is of use in generating an immune response, such as a macrophage, neutrophil, granulocyte, dendritic cell, T- and/or B cell-mediated response. In addition, an inhibitor of extracellular adenosine and adenosine receptor inhibitors are of use in promoting acute or chronic inflammation. Inhibitors of the Gs protein mediated cAMP dependent intracellular pathway and inhibitors of the adenosine receptor-triggered $G_i$ protein mediated intracellular pathways, can also be used to increase acute and chronic inflammation.

Figure 16:
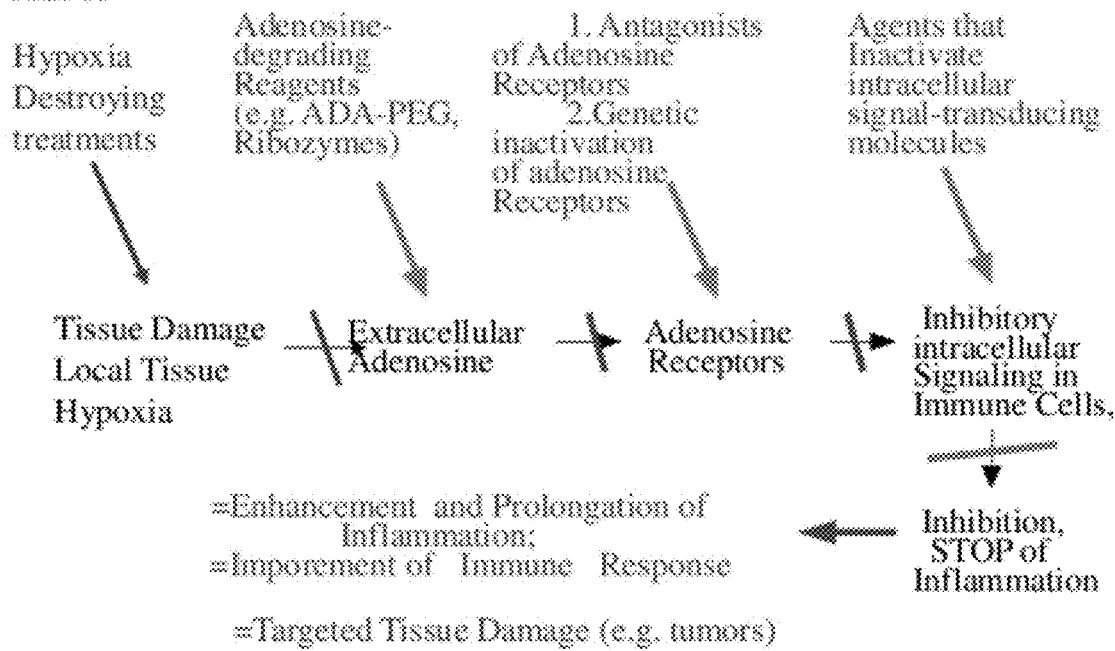
FIG. 16 is a summary of the methods that can be used to enhance and/or prolong inflammatory responses by inhibiting or decreasing the endogenous anti-inflammatory processes.

Inhibitors of: Adenosine Receptors, the Intracelluar Camp Dependent Pathway and Extracellular Adenosine Disclosed herein are methods for increasing an immune response or inflammation, and methods for targeted tissue damage, by contacting an immune cell or administering to a subject, one or more agents that inhibit extracellular adenosine or adenosine receptor inhibitors, such as adenosine receptor antagonists. A summary is provided in FIG. 16.

An agent that inhibits extracellular adenosine includes agents that render extracellular adenosine non-functional (or decrease such function), such as a substance that modifies the structure of adenosine to nullify the ability of adenosine to signal through adenosine receptors. This can be, for example, an enzyme (e.g. adenosine deaminase) or another catalytic molecule that selectively binds and destroys the adenosine, thereby abolishing or significantly decreasing the ability of endogenously formed adenosine to signal through adenosine receptors and terminate inflammation. One agent that degrades extracellular adenosine is ADA-PEG, polyethylene glycol-modified ADA that has been used in treatment of patients with ADA SCID (Hershfield, *Hum Mutat.* 5:107, 1995). In another example, an agent that inhibits extracellular adenosine includes agents that prevent or decrease formation of extracellular adenosine, and/or prevent or decrease the accumulation of extracellular adenosine.

Adenosine receptor inhibits include adenosine receptor antagonists. An antagonist is any substance that tends to nullify the action of another, as an agent that binds to a cell receptor without eliciting a biological response. In one example, the antagonist is a chemical compound that is an antagonist for an adenosine receptor, such as the A2a, A2b, or A3 receptor. In another example, the antagonist is a peptide, or a pepidomimetic, that binds the adenosine receptor but does not trigger a G1 protein dependent intracellular pathway. Suitable antagonists are described in U.S. Pat. Nos. 5,565,566; 5,545,627, 5,981,524; 5,861,405; 6,066,642; 6,326,390; 5,670,501; 6,117,998; 6,232,297; 5,786,360; 5,424,297; 6,313,131, 5,504,090; and 6,322,771.

In another example, the antagonist is an antisense molecule or catalytic nucleic acid molecule (e.g. a ribozyme) that specifically binds mRNA encoding an adenosine receptor. In specific, non-limiting examples, the antisense molecule or catalytic nucleic acid molecule binds A2a, A2b, or A3. In a further example, an antisense molecule or catalytic nucleic acid targets biochemical pathways downstream of the adenosine receptor. For example, the antisense molecule or catalytic nucleic acid can inhibit an enzyme involved in the Gs protein- or Gi protein-dependent intracellular pathway.

Adenosine receptor protein expression in a host cell can be reduced by introducing into cells an antisense construct or another genetic sequence-targeting agent, based on an adenosine receptor locus, e.g. the adenosine receptor A1, A2a, A2b, or A3 locus (e.g. Genbank accession numbers L22214, AH003248, NM000676, and AH003597, respectively). An antisense construct includes the reverse complement of the adenosine receptor cDNA coding sequence, the adenosine receptor cDNA or gene sequence or flanking regions thereof. For antisense suppression, a nucleotide sequence from the adenosine receptor locus (e.g. all or a portion of the adenosine receptor cDNA or gene or the reverse complement thereof) is arranged in reverse orientation relative to the promoter sequence in a vector. The vector is then introduced into a cell of interest. Where the reverse complement of the reported sequences is used to suppress expression of proteins from the adenosine receptor locus, the sense strand of the disclosed adenosine or adenosine receptor locus or cDNA is inserted into the antisense construct. Without being bound by theory, it is believed that antisense RNA molecules bind to the endogenous mRNA molecules and thereby inhibit translation of the endogenous mRNA.

For suppression of an adenosine receptor gene, transcription of an antisense construct results in the production of RNA molecules that are the reverse complement of mRNA molecules transcribed from the endogenous adenosine receptor gene in the cell. The introduced sequence need not be the full-length human adenosine receptor cDNA or gene or reverse complement thereof, and need not be exactly homologous to the equivalent sequence found in the cell type to be transformed. Generally, however, where the introduced sequence is of shorter length, a higher degree of homology to the native adenosine or adenosine receptor locus sequence is needed for effective antisense suppression. In one example, the introduced antisense sequence in the vector is at least 10, such as at least 30 nucleotides in length. Improved antisense suppression is typically observed as the length of the antisense sequence increases. Shorter polynucleotide (oligonucleotides) can conveniently be produced synthetically as well as in vivo. In specific aspects, the oligonucleotide is at least 10 nucleotides, at least 15 nucleotides, at least 30, at least 100 nucleotides, or at least 200 nucleotides.

To inhibit the translation of the target RNA molecule, such as an adenosine receptor, the antisense molecule will ideally persist in the cell for a sufficient period to contact the target RNA. However, cells contains enzymes and other components that cause polynucleotides (such as an antisense molecule) to degrade. The antisense molecule can be engineered such that it is not degraded in the cell. This can be done, for example, by substituting the normally occurring phosphodiester linkage which connects the individual bases of the antisense molecule with modified linkages. These modified linkages can, for example, be a phosphorothioate, methylphosphonate, phosphodithioate, or phosphoselenate. Furthermore, a single antisense molecule can contain multiple substitutions in various combinations.

The antisense molecule can also be designed to contain different sugar molecules. For example the molecule can contain the sugars ribose, deoxyribose or mixtures thereof, which are linked to a base. The bases give rise to the molecules' ability to bind complementarily to the target RNA. Complementary binding occurs when the base of one molecule forms a hydrogen bond with another molecule. Normally the base adenine (A) is complementary to thymidine (T) and uracil (U), while cytosine (C) is complementary to guanine (G). Therefore, the sequence ATCG of the antisense molecule will bond to TAGC of the target RNA. Additionally, the antisense molecule does not have to be 100% complementary to the target RNA to be effective.

The oligonucleotides can be DNA or RNA, or chimeric mixtures or derivatives or modified versions thereof, single-stranded or double-stranded. The oligonucleotide can be modified at the base moiety, sugar moiety, or phosphate backbone, and can include other appending groups such as peptides, or agents facilitating transport across the cell membrane (see, e.g., Letsinger et al., *PNAS USA* 86:6553-6, 1989; Lemaitre et al., *PNAS USA* 84:648-52, 1987; PCT Publication No. WO 88/09810) or blood-brain barrier (see, e.g., PCT Publication No. WO 89/10134), hybridization triggered cleavage agents (see, e.g., Krol et al., *BioTechniques* 6:958-76, 1988) or intercalating agents (see, e.g., Zon, *Pharm. Res.* 5:539-49, 1988).

In a particular example, an adenosine receptor antisense polynucleotide is provided, for example as a single-stranded DNA. Such a polynucleotide can include a sequence antisense to a sequence encoding an A1, A2a, A2b, or A3 receptor. The oligonucleotide can be modified at any position on its structure with substituents generally known in the art. For example, a modified base moiety can be 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine.

In another example, the polynucleotide includes at least one modified sugar moiety such as arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

The antisense polynucleotide can be conjugated to another molecule, for example a peptide, hybridization triggered cross-linking agent, transport agent, or hybridization-triggered cleavage agent. A targeting moiety can also be included that enhances uptake of the molecule by tumor cells. The targeting moiety can be a specific binding molecule, such as an antibody or fragment thereof that recognizes a molecule present on the surface of the tumor cell.

Suppression of endogenous adenosine receptor locus expression can also be achieved using catalytic nucleic acids such as ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. Ribozymes can be synthesized and administered to a cell or a subject, or can be encoded on an expression vector, from which the ribozyme is synthesized in the targeted cell (as in PCT publication WO 9523225, and Beigelman et al. *Nucl. Acids Res.* 23:4434-42, 1995). Examples of oligonucleotides with catalytic activity are described in WO 9506764, WO 9011364, and Sarver et al. (*Science* 247:1222-5, 1990). The inclusion of ribozyme sequences within antisense RNAs can be used to confer RNA cleaving activity on the antisense RNA, such that endogenous mRNA molecules that bind to the antisense RNA are cleaved, which in turn leads to an enhanced antisense inhibition of endogenous gene expression.

In addition, dominant negative mutant forms of an adenosine receptor can be used to block endogenous adenosine receptor activity. In this example, a nucleic acid encoding a dominant negative mutant form of an adenosine receptor is operably linked to a promoter. In one specific, non-limiting example, the promoter is an inducible promoter. A vector containing the promoter and the nucleic acid encoding the dominant negative adenosine receptor is than introduced into a cell.

In another example, local tissue accumulation of extracellular adenosine is inhibited using a preparation of adenosine deaminase (ADA). This can be, for example, an enzyme, adenosine deaminase or a ribozyme, or another catalytic molecule that selectively binds and destroys adenosine, thereby abolishing, or substantially decreasing, the ability of endogenously-formed adenosine to signal through adenosine receptors and terminate inflammation.

The propagation of adenosine receptor-triggered intracellular signaling cascade can also be affected by the use of specific inhibitors of enzymes and proteins that are involved in regulation of synthesis and/or secretion of pro-inflammatory molecules, including modulators of nuclear transcription factors.

Suppression of adenosine receptor expression or expression of the Gs protein- or Gi protein-dependent intracellular pathway, or the cAMP dependent intracellular pathway, are also used to increase/enhance inflammation or the immune response in a variety of situations (see below).

Increasing an Immune Response

Methods are disclosed herein to enhance and prolong the pro-inflammatory response by blocking the natural, extracellular adenosine-dependent, endogenous anti-inflammatory processes in vivo using an adenosine receptor inhibitor and/or an inhibitor of extracellular adenosine. In one example, the adenosine receptor is A2a, A2b, or the A3 receptor.

Also disclosed herein is a method for increasing an activity of an immune cell. Immune cells include, but are not limited to: leukocytes (i.e. neutrophils, eosinophils, lymphocytes, monocytes, basophils, macrophages, B cells, T cells, dendritic cells, and mast cells), as well as other types of pro-inflammatory cytokine-producing cells. In another example, the immune cell is a macrophage. In yet another example, the immune cell is an antigen-presenting dendritic cell. In a further embodiment, the immune cell is a natural killer cell. In an additional example, the immune cell is a granulocyte. The immune cell activity can be increased either in vivo or in vitro. In one example, this method includes targeting adenosine receptors on any other cell that produces pro-inflammatory cytokines/molecules, including those that are not considered "classical immune cells."

Thus, in one specific, non-limiting example the cell is a B cell, and secretion of an immunoglobulin (e.g. IgG or IgM) is increased. In another specific, non-limiting example the cell is a T cell and the activity is secretion of a cytokine (e.g. IL-2 or IL-4) is increased. Similarly, in another embodiment the cell is either a helper T cell or a cytotoxic T cell, and either the helper T cell functions or the cytotoxic T cell functions are increased. Without being bound by theory, cytotoxic T cell activities are increased due to longer expression of lethal hit delivering Fas Ligand molecules or due to better trafficking of immune cells toward the targeted tissue in vivo. Without being bound by theory, T helper cell activities are enhanced because of prolonged secretion of cytokines.

The method includes contacting the immune cell with an adenosine receptor inhibitor, such as an adenosine receptor antagonist, or an inhibitor of extracellular adenosine, thereby increasing the activity of the immune cell. The immune cell can be involved in an acute immune response or in a chronic immune response.

One of skill in the art can readily identify methods of use in identifying an increased activity of an immune cell. For example, secretion of cytokines can be measured by ELISA or PCR-based assays or in biological assays. In one example, the increase in activity is measured as compared to a control. Suitable controls include an immune cell not contacted with an adenosine antagonist, or a standard value.

A method is disclosed herein for enhancing an immune response in a subject. The method includes administering to the subject a therapeutically effective dose of an adenosine receptor inhibitor and/or an inhibitor of extracellular adenosine, to enhance the immune response. In one example, the immune response is a macrophage/monocyte or B cell response. In another example the immune response is a T cell response.

A method is provided herein for improving a T cell mediated immune response. The method includes the administration of an adenosine receptor inhibitor and/or an inhibitor of extracellular adenosine, to a subject. In one embodiment, the subject is an immunosuppressed subject, such as a subject infected with an immunodeficiency virus (e.g. HIV-1 or HIV-2). The administration of the adenosine receptor inhibitor and/or an inhibitor of extracellular adenosine results in an increase in a desired immune response and/or prolonged secretion of a cytokine of interest. In another example, the subject is infected with a pathogen such as a bacterial, viral, or fungal pathogen. Adenosine receptor inhibitors and/or inhibitors of extracellular adenosine are administered to facilitate pathogen destruction in the subject. In one example, the subject is immunosuppressed. Immune deficiencies (e.g. deficiencies of one or more type of immune cells, or of one or more immunological factors) associated with immune deficiency diseases, immune suppressive medical treatment, acute and/or chronic infection, and aging can be treated using the methods described herein. A general overview of immunosuppressive conditions and diseases can be found in Harrisons "Principles of Internal Medicine," $14^{th}$ Edition, McGraw-Hill, 1998, and particularly in chapter 86 (Principles of Cancer Therapy), chapter 307 (Primary Immune Deficiency Diseases), and chapter 308 (Human Immunodeficiency Virus Diseases).

Many medical treatments can impair the immune system. Corticosteroids, for example, can reduce cell-mediated immunity. The predominant toxicity associated with cancer therapies (e.g. chemotherapy and radiotherapy) is destruction of proliferating cells, such as hematopoietic cells, responsible for maintenance of the immune and blood systems Likewise, immune suppression and depletion of the immune system is required for bone marrow transplantation, in which immune cells are eliminated and subsequently replaced with transplanted cells. Certain known immunostimulants (e.g. erythropoietin and colony stimulating factors such as G-CSF, which is sometimes marketed under the name "Neupogen," U.S. Pat. No. 5,536,495) have been used previously to treat certain of these conditions by stimulating regeneration of the immune cells. The immunostimulatory compounds and mixtures of the disclosure can be used to stimulate the immune systems of patients suffering from medical treatment or iatrogenically induced immune suppression, including those who have undergone bone marrow transplants, chemotherapy, and/or radiotherapy.

Other conditions are known in which the immune system is compromised or suppressed. For example, activation of the immune system (via stimulation of T cell production) by adenosine receptor antagonist treatment can also be beneficial in aging subjects, in whom immune function is often compromised. Similarly, other conditions are known in which the immune response is abnormal or undesirable. Any of these conditions would also benefit from the methods disclosed herein, or application of the described compositions. In general, the need for treatment with one of the methods or compositions of this disclosure can be determined by examining the immune status of a test subject, and comparing this immune status to a control or average immune state (a hypothetical "normal" subject). For example, bone marrow biopsies or peripheral blood lymphocytes can be sampled to assess immune function. Indications of reduced immune function include leukopenia, for example neutrophenia or lymphopenia, or evidence of diminished white blood cell function. Where the test subject has a reduced immunity condition, such as a reduction in a peripheral white blood cell count to below normal, for example 25% below normal, the immunostimulatory methods of the disclosure should be considered as treatments to improve the immune suppressed condition.

Also disclosed are methods that can be used to enhance NF-kB activity in a subject, by administering to a subject an adenosine receptor inhibitor and/or an inhibitor of extracellular adenosine. Enhancement of NF-kB activity, promotes transcription of pro-inflammatory cytokines, such as IL-12p40 and TNF-α, thereby increasing an immune response.

Vaccines

A method is provided for increasing an immune response to an antigen by providing an adjuvant activity. To increase an immune response to an antigen, the antigen is administered in conjunction with an inhibitor of extracellular adenosine, an adenosine receptor inhibitor, an inhibitor of the intracellular cAMP dependent pathway, and/or an inhibitor of intracellular Gi protein dependent pathway, which functions as an adjuvant.

In one example, a method for prolonging an immune response to a vaccine is provided. The method includes administering an adenosine receptor inhibitor in conjunction with the vaccine, such as an adenosine receptor antagonist.

Thus, disclosed herein is the use of an adenosine receptor inhibitor, such as an adenosine receptor antagonist, in adjuvant formulations. Methods for the stimulation of an immune response to a particular antigen are thus also within the scope of the disclosure. The host animals to which the adjuvant and adjuvant-containing vaccine formulations of the present disclosure are usefully administered include human as well as non-human mammals.

Typically, an antigen is employed in mixture with the adjuvant compounds of the disclosure. Therapeutic adjuvant formulations are disclosed herein which, for example, include (i) at least one therapeutically effective antigen or vaccine; and (ii) at least one adenosine receptor antagonist or adenosine degrading drug (e.g. ADA-PEG).

Such therapeutic composition can for example include at least one antigenic agent such as (A) live, heat killed, or chemically attenuated viruses, bacteria, mycoplasmas, fungi, and protozoa; (B) fragments, extracts, subunits, metabolites and recombinant constructs of (A); (C) fragments, subunits, metabolites and recombinant constructs of mammalian proteins and glycoproteins; (D) tumor-specific antigens; and (E) nucleic acid vaccines.

The therapeutic composition can therefore utilize any suitable antigen or vaccine component in combination with an adenosine receptor antagonist e.g. an antigenic agent, such as antigens from pathogenic and non-pathogenic organisms, viruses, and fungi, in combination with an adjuvant compound of the disclosure.

As a further example, such therapeutic compositions can suitably include proteins, peptides, antigens and vaccines which are pharmacologically active for disease states and conditions such as smallpox, yellow fever, distemper, cholera, fowl pox, scarlet fever, diphtheria, tetanus, whooping cough, influenza, rabies, mumps, measles, foot and mouth disease, and poliomyelitis. In the resulting vaccine formulation, comprising (i) an antigen, and (ii) at least one adenosine receptor inhibitor or and inhibitor of extracellular adenosine, the antigen and adjuvant compound are each present in an amount effective to elicit an immune response when the formulation is administered to a host animal, embryo, or ovum vaccinated therewith (see below).

Tumor Treatment

The importance of lymphoid cells in tumor immunity has been repeatedly shown. A cell-mediated host response to tumors includes the concept of immunologic surveillance, by which cellular mechanisms associated with cell-mediated immunity destroy newly transformed tumor cells after recognizing tumor-associated antigens (antigens associated with tumor cells that are not apparent on normal cells). This is analogous to the process of rejection of transplanted tissues from a non-identical donor. In humans, the growth of tumor nodules has been inhibited in vivo by mixing suspensions of a patient's peripheral blood lymphocytes and of tumor cells, suggesting a cell-mediated reaction to the tumor. In vitro studies have shown that lymphoid cells from patients with certain neoplasms show cytotoxicity against corresponding human tumor cells in culture. These cytotoxic cells, which are generally T-cells, have been found with neuroblastoma, malignant melanomas, sarcomas, and carcinomas of the colon, breast, cervix, endometrium, ovary, testis, nasopharynx, and kidney. Humoral antibodies that react with tumor cells in vitro have also been produced in response to a variety of animal tumors induced by chemical carcinogens or viruses. Hybridoma technology in vitro permits the detection and production of monoclonal anti-tumor antibodies directed against a variety of animal and human neoplasms. Antibody-mediated protection against tumor growth in vivo has been demonstrable in both leukemias and lymphomas.

A method is provided herein to increase inflammatory actions of immune cells including tumor-infiltrating lymphocytes, and in some embodiments, to additionally promote the recruitment of other immune cells with anti-tumor activity to improve the destruction of the tumor (such as reducing the size or volume of the tumor). A method is provided to improve both natural anti-cancer immune response and adaptive immunotherapy of cancer by immune cells that recognize tumor-associated antigens on the tumor cell surface. In one example, a first agent is administered to a subject that has an affinity (tropism) for tumor cells. A second agent that is an adenosine receptor inhibitor (such as adenosine receptor antagonist) and/or an inhibitor of extracellular adenosine, is administered to the subject to promote the immune response against the tumor. Without being bound by theory, the first agent selectively accumulates in the tumor due to tropism for the to tumor cells or the local environment. The first agent initiates the death of some low proportion of tumor cells due to its own cytotoxicity against tumor cells.

In one example, the first agent induces cell death in the tumor cells. In an additional example, the first agent is a chemotherapeutic agent. In yet another embodiment, the first agent initiates an immune response directed against the tumor cells. In one example, the second agent is a genetic targeting agent used to mutate an adenosine receptor such that the receptor does not bind adenosine, or does not activate the biochemical pathway triggered by the adenosine receptor. It is shown herein that by triggering low levels of inflammation in targeted tissues (e.g. tumors) with a first agent, in addition to complementary inactivation of adenosine receptors or decreasing extracellular adenosine using genetic or pharmacological techniques, results in destruction of the tissue (e.g tumor).

In one example, the first agent is an immunotoxin that accumulates in the tumor due to their selective interactions with tumor-specific antigens. These reagents cause direct destruction of tumor cells, although destruction of the tumor is not complete. Without being bound by theory, the death of a portion of the tumor cells creates an inflammatory environment within the tumor and activates tumor infiltrating immune cells (macrophages and T cells). The natural inhibitory pathway which would prematurely terminate this anti-tumor activity will be then interrupted by the adenosine receptor inhibitor (such as adenosine receptor antagonist) or an inhibitor of extracellular adenosine (such as an extracellular adenosine degrading or disrupting agent). Thus, administration of a inhibitor of an adenosine receptor and/or an inhibitor of extracellular adenosine, exacerbates tumor cell death.

In another example, the first compound initiates the anti-tumor process in vivo. A bi-functional immune cell activating reagent is coupled to an antibody that binds a tumor specific antigen and to a T cell or macrophage-activating ligand (e.g. anti-T cell receptor mAb or T cell-like receptor ligand, respectively). Without being bound by theory the first agent accumulates in the tumor due to its selective interactions with tumor-specific antigens. The first agent also directs activation of tumor infiltrating immune cells, which destroys tumor cells. This activation of immune cells and tumor cells death will creates an inflammatory environment within the tumor and also activates tumor infiltrating immune cells (e.g. macrophages and T cells). The second agent is an adenosine receptor inhibitor (such as an adenosine receptor antagonist) or an inhibitor of extracellular adenosine that exacerbates tumor cell death.

In another embodiment, the first agent initiates an antitumor process in vivo is a population of T cells that are specific for tumor antigens, alone or in combination with other ligands that enhance antitumor activity of T cells (e.g. CTLA-4 ligand; Kuhns et al., *Proc. Natl. Acad. Sci. USA* 97:12711, 2001) or in combination with the removal of $CD25^+$ regulatory T cells. Depletion of either of these two immunoregulatory mechanisms improves anti-tumor CTL activity (Sutmuller et al., *J. Exp. Med.* 94:823-32, 2001). Without being bound by theory, this activation of immune cells and tumor cells death creates an inflammatory environment within the tumor and activates tumor infiltrating immune cells (macrophages and T cells). In this example, the second agent is not an adenosine receptor antagonist or adenosine degrading agent. Instead, it is the process of preparing anti-tumor immune cells under conditions that lead to the loss of (or reduction of) adenosine receptors, and thereby renders these cells uninhabitable by tumor-associated adenosine. This process can include additional conditions, such as hypoxic incubators to increase endogeneous adenosine formation in cell cultures, or addition of adenosine analogs to provide selective negative pressure to prevent or decrease expansion of adenosine receptor-expressing immune cells.

In an additional embodiment, the first agent is a cytotoxic compound that accumulates in tumor because of differences between tumor and normal tissue environment (e.g. differences in growth rate, redox potential or oxygen tension (hypoxia) or other chemical differences). Without being bound by theory, this compound causes tumor cell death and creates an inflammatory environment within the tumor and further activates tumor infiltrating immune cells (macrophages and T cells). The second agent is an adenosine receptor inhibitor (such as an adenosine receptor antagonist) or an inhibitor of extracellular adenosine, that exacerbates tumor cell death by preventing or decreasing the inactivation of anti-tumor cells by adenosine.

In yet another embodiment, the first agent is a compound that accumulates in tumor cells and is cytotoxic due to the increased proliferation of tumor cells Without being bound by theory, this compound causes tumor cell death and creates an inflammatory environment within the tumor. Tumor infiltrating immune cells (macrophages and T cells) are activated. The second agent is an adenosine receptor inhibitor (such as an adenosine receptor antagonist) or an inhibitor of extracellular adenosine (such as an extracellular adenosine degrading agent) that exacerbates tumor cell death.

Pharmaceutical Compositions and Administration

Pharmaceutical compositions that include at least one adenosine receptor inhibitor, such as an adenosine receptor antagonist, and/or at least one inhibitor of extracellular adenosine, can be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate.

Other medicinal and pharmaceutical agents, for instance another immunostimulant, also can be included. Immunostimulants include, but are not limited to, IFA, COX-2 inhibitors, IL-12, saponins (e.g. QS-23), and N-acetyl-cysteine, for example.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations can be liquid (e.g. syrups, solutions or suspensions), or solid (e.g. powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that comprise an adenosine receptor antagonist in some embodiments of the disclosure will be formulated in unit dosage form, suitable for individual administration of precise dosages. For example, one possible unit dosage can contain from about 1 mg to about 1 g of adenosine receptor agonist or antagonist. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The compounds of this disclosure can be administered to humans or other animals on whose cells they are effective in various manners such as topically, orally, intravenously, intramuscularly, intraperitoneally, intranasally, transdermally, intradermally, intrathecally, and subcutaneously. The particular mode of administration and the dosage regimen will be selected by the attending clinician, taking into account the particulars of the case (e.g. the subject, the disease, the disease state involved, and whether the treatment is prophylactic). Treatment can involve daily or multi-daily doses of compound(s) over a period of a few days to months, or even years.

A therapeutically effective amount of an adenosine receptor inhibitor and/or an inhibitor of extracellular adenosine, can be the amount of adenosine receptor antagonist necessary to stimulate the immune system of a subject. Specific immunostimulatory effects that can be caused by adenosine receptor antagonists as well as specific immunosuppressive effects that can be caused by adenosine receptor agonists are described herein. In some embodiments, an immunostimulatory amount of an adenosine receptor antagonist is an amount sufficient to stimulate an immune response (for instance, any of the stimulatory responses discussed herein) without causing a substantial cytotoxic effect (e.g. without killing more than 10% of cells in a sample).

An effective amount of an adenosine receptor inhibitor and/or an inhibitor of extracellular adenosine can be administered in a single dose, or in several doses, for example daily, during a course of treatment. However, the effective amount of an adenosine receptor inhibitor and/or an inhibitor of extracellular adenosine will be dependent on the specific agonist or antagonist applied, the subject being treated, the severity and type of the affliction, and the manner of administration of the therapeutic(s). For example, a therapeutically effective amount of an adenosine receptor inhibitor and/or an inhibitor of extracellular adenosine can vary from about 0.1 mg/Kg body weight to about 1 g/Kg body weight.

Site-specific administration of the disclosed compounds can be used, for instance by applying an adenosine receptor antagonist to a precancerous region, a region of tissue from which a neoplasm has been removed, or a region suspected of being prone to neoplastic development.

The present disclosure also includes combinations of an adenosine receptor inhibitor and/or an inhibitor of extracellular adenosine, with one or more other agents useful in the treatment of an immune-related disorder, condition, or disease. For example, the compounds of this disclosure can be administered in combination with effective doses of other immunosuppressives, immunostimulants, anti-cancer agents, anti-inflammatories, anti-infectives, and/or vaccines. The term "administration in combination" or "co-administration" refers to both concurrent and sequential administration of the active agents. In one example, SEQ ID NO: 1 is co-administered with an adenosine receptor inhibitor and/or an inhibitor of extracellular adenosine. In another example SEQ ID NO: 1 is administered before or after administration of an adenosine receptor inhibitor and/or an inhibitor of extracellular adenosine.

Examples of agent that can be used in combination with the compounds of the disclosure are AS-101 (Wyeth-Ayerst Labs.), bropirimine (Upjohn), gamma interferon (Genentech), GM-CSF (Genetics Institute), IL-2 (Cetus or Hoffman-LaRoche), human immune globulin (Cutter Biological), IMREG (from Imreg of New Orleans, La.), SK&F106528 (Genentech), TNF (Genentech), azathioprine, cyclophosphamide, chlorambucil, and methotrexate. Treatment of a subject using the immunostimulatory compositions of the disclosure can be indicated after (or while) the subject has received an anti-proliferative or other cytotoxic therapeutic treatment. Examples of anti-proliferatives compounds include the following: ifosamide, cisplatin, methotrexate, cytoxan, procarizine, etoposide, BCNU, vincristine, vinblastine, cyclophosphamide, gencitabine, 5-fluorouracie, paclitaxel, and doxorubicin.

In some examples, a subject is administered a cytotoxic treatment, then monitored for a period of time (usually in the range of days to weeks) to determine if the treatment leads to an immunosuppressive effect. Such monitoring can include monitoring peripheral blood for leukopenia or pancytopenia, and/or monitoring T cell function. A subject that displays an immune suppression will be a candidate for treatment using the therapeutic methods of the disclosed disclosure.

Methods for Screening for Adenosine Receptor Antagonists

Also disclose are methods for screening for adenosine receptor antagonist effects using a cell of the immune system. The method includes contacting an activated immune cell with the compound, and assaying the activity of the immune cell. An increase in activity or a prolonged period of activation of the immune cell indicates that the compound is an adenosine receptor antagonist, which is efficient in an in vivo setting. Such methods can also be used to screen for immunosuppressants and immunostimulants, wherein increased activity or a prolonged period of activation of the immune cell indicates that the compound is an immunostimulant, and wherein decreased activity or a reduction in the period of activation of the immune cell indicates that the compound is an immunosuppressant.

Among other uses, functional assays of receptor antagonist function permit optimization of the dosage amounts of each receptor agonist or antagonist effective in therapeutic uses. These assays can also be used to test known adenosine receptor antagonists, as well as newly identified adenosine receptor antagonists or putative adenosine receptor antagonists for immunosuppressive or immunostimulatory bioactivity. Candidate agents can initially be screened for subsequent selection and testing in one or more of the assays described herein.

Adenosine receptor antagonist immunostimulatory activity is the ability of an adenosine receptor antagonist to enhance an immune response in an immune cell, an immune system, and/or more generally in a subject. More specifically, adenosine receptor antagonist-related immunostimulation includes those effects that can be seen when an adenosine receptor antagonist is applied to an in vitro system using a dosage of less than 2 µg/ml, and more particularly when less than 1 µg/ml (e.g., about 0.1 µg/ml to as little as 0.003 µg/ml or less). In an in vivo system, these effects are seen at an application level of about 1 µg to about 5 µg in a 20 g mouse, or about 50 to about 250 µg/Kg body weight. Specific immunostimulatory effects that can be involved include stimulation of T-cell production, stimulation of interleukin production (e.g. production of IL-1 and/or IL-12 by macrophages), and activation of natural killer cells and/or macrophages.

Methods for examining adenosine receptor inhibitor-mediated immunostimulation include those disclosed herein, such as direct measurement of the activation or proliferation of one or more immune cell types, or increased (or decreased) interleukin production (e.g. IL-1 or IL-12). Secondary effects of immune stimulation can also be measured as described herein, for instance by examining the formation of tumors, the relative rate of growth of a tumor, or tumor metastasis, or by resistance of an organism treated with the test compound to viral or other infection.

Example 1

Activation of A2a Receptors Reduces Concanavalin-A-Induced Liver Damage In Vivo

This example describes methods that were used to demonstrate that pharmacological activation of A2a receptors by a selective A2a agonist prevents liver damage in a model of inflammatory liver injury.

Concanavalin A (Con-A)-induced liver injury in mice is mediated by T-cells, macrophages and pro-inflammatory cytokines TNF-$\alpha$, IL-4 and IFN-$\gamma$, and represents a well-described in vivo inflammation model of viral and autoimmune hepatitis. Five B6 wild type mice were injected intravenously (i.v.) with 20 mg/kg Con A (type IV, Sigma, St. Louis, Mo.) in sterile PBS alone or co-injected intraperitoneally (i.p.) with CGS21680 (2 mg/kg), isoproterenol (100 mg/kg, Sigma, St. Louis, Mo.), or prostaglandin $E_2$ ($PGE_2$, 5 mg/kg, Sigma, St. Louis, Mo.) just before Con A treatment. The extent of liver damage and inflammation were quantified by measuring serum levels of liver enzyme alanine aminotransferase (ALT) and TNF-$\alpha$ at 1.5 hours, 4 hours, and 8 hours after Con-A injection. TNF-$\alpha$ was measured using an ELISA kit (R&D systems, Minneapolis, Minn.) according to manufacturer suggestions. Serum ALT activity was determined using a colorimetric assay kit (Sigma, St. Louis, Mo.).

The data disclosed herein are expressed as mean+/−s.e.m. Differences between groups were evaluated using Student's t-test.

Figure 1B:
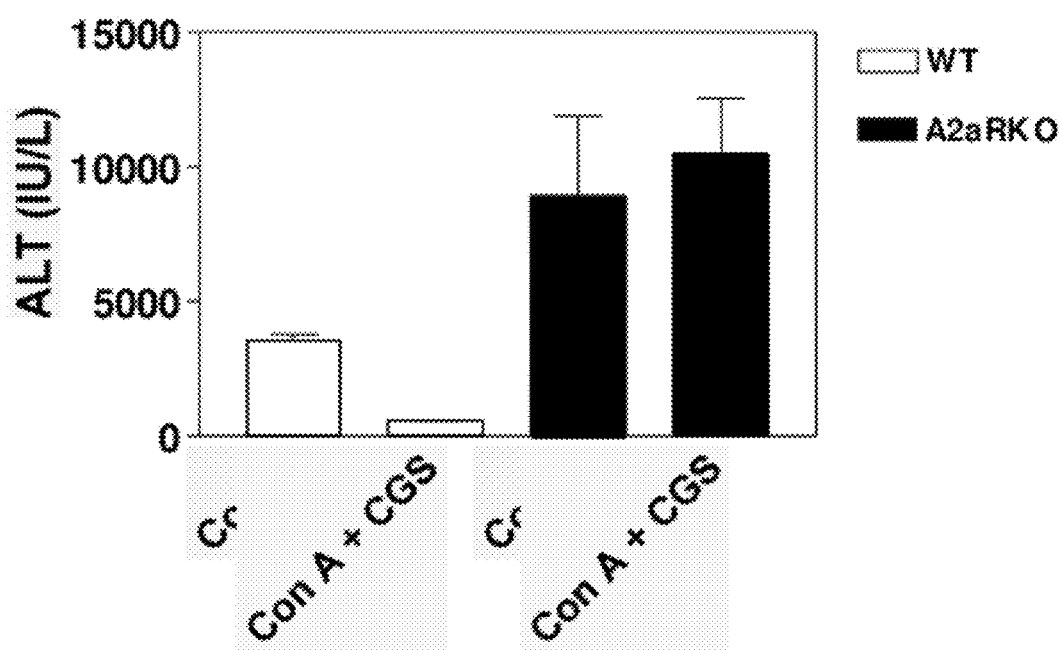
FIG. 1B is a bar graph showing that pharmacologically activated cAMP-elevating A2a receptors are capable of blocking inflammation in vivo. The differences between treated and untreated mice are statistically significant as indicated by the asterisk (*P<0.05).

As shown in FIG. 1A, pharmacological activation of several cAMP-elevating $G_s$-coupled receptors prevented or reduced liver damage. Similarly, activation of A2a, inhibited Con-A-induced pro-inflammatory TNF-α accumulation in vivo. The A2a agonist, CGS21680, also inhibited secretion of IL-12 and IFN-γ by activated macrophages and T cells in vitro as measured using an ELISA kit (R&D systems, Minneapolis, Minn.) (FIG. 1B). Therefore, pharmacological activation of A2a receptors or other $G_s$-protein-coupled receptors in vivo prevents or reduces Con-A-induced liver damage and pro-inflammatory TNF-α accumulation.

Example 2

Effect of A2a Agonists and Antagonists on Camp Levels in Mouse Liver Mononuclear Cells In Vitro This example describes methods that were used to demonstrate that A2a receptor signaling (cAMP accumulation) is decreased or even abolished in liver mononuclear cells and macrophages from A2aR$^{-/-}$ mice but not in cells from A2a$^{+/+}$ littermates.

Littermates or age-matched wild type (A2aR$^{+/+}$) and homozygous A2a receptor gene deficient mice (A2aR$^{-/-}$) were used in all experiments for better reproducibility of results. C57BL/6-background A2a receptor-deficient mice have been described previously (Chen et al., *J. Neuroscience* 19:9192-9200, 1999; Apasov et al., *Br. J. Pharmacol.* 131: 43-50, 2000; and Armstrong et al., *Biochem. J.* 354:123-130, 2001). The A2a receptor genotypes of mice were determined by Southern blot analysis (Chen et al., *J. Neuroscience* 19:9192-200, 1999).

Stimulation of cells and measurement of cAMP levels were carried out as described previously (Apasov et al., *Br. J. Pharmacol.* 131:43-50, 2000, herein incorporated by reference). Briefly, liver mononuclear cells were isolated from parenchymal hepatocytes and cell debris using Percoll (Amersham Pharmacia Biotech, Uppsala, Sweden). The resulting liver mononuclear cells ($1 \times 10^5$ cells/200 μl) were incubated at 37° C. for 30 minutes in the presence of 10 μM CGS21680, 1 μM ZM241385 (Tocris, Ballwin, Mo.), 100 μM isoproterenol, 50 μM forskolin, or 1 μM $PGE_2$. The cAMP levels were determined using a cAMP enzyme immunoassay kit according to the manufacturer's instructions (Amersham Pharmacia Biotech, Buckinghamshire, England, UK).

As shown in FIG. 2A, the A2aR antagonist, ZM241385, inhibited AGORA2a agonist (CGS21680)-induced cAMP increase in mononuclear cells from A2aR$^{+/+}$ mouse livers. By contrast, the A2aR agonist, CGS21680, did not increase cAMP in mononuclear cells from A2aR$^{-/-}$ mouse livers (FIG. 2B). Cells from A2aR$^{-/-}$ mice retained the cAMP response to ligands of other Gs protein coupled receptors (FIG. 2D). Therefore, A2a receptors can downregulate inflammation when activated by agonists. Therefore, there is a deficiency in cAMP-elevating receptors in A2a deficient mice. As a result, these mice can be used to establish the role of A2a receptors in inflammation in vivo.

Example 3

Accumulation of Inflammatory Cytokines and Liver Damage in A2a-Receptor-Deficient Mice This example describes methods that were used to demonstrate that the absence of functional A2a receptors results in increased inflammation and exacerbated tissue damage, in response to administration of Con-A.

A2a$^{+/+}$ (n=5) and A2a receptor gene deficient (A2a$^{-/-}$) mice (n=5) were used. Mice were injected intravenously with a sub-optimal dose (12.5 mg/kg) of Con-A (see inset, FIG. 3A), and subsequently, serum levels of ALT and cytokines were measured at 1, 6, 8, 24, and 48 hours as described in EXAMPLE 1 (cytokines were measured using an ELISA kit (R&D systems) according to manufacturer suggestions).

As shown in FIG. 3A, a large increase in serum ALT levels in A2a mice as compared to A2a$^{+/+}$ mice was observed following Con-A treatment. Even a sub-optimal dose of inflammatory stimuli, Con-A (see inset to FIG. 3A) resulted in the death of two out of five A2aR$^{-/-}$ mice within 48 hours, while all A2aR$^{+/+}$ controls survived. Low doses of Con-A, which caused only minimal or no liver damage in control A2aR$^{+/+}$ mice, were sufficient to induce extensive inflammation and liver damage in A2aR$^{-/-}$ mice, as evidenced accumulation of dead cells and leukocytes using TdT apoptosis test and haematoxylin and eosin (H-E) stain.

The effect of TNF-α on liver injury in A2aR$^{+/+}$ (n=5) and A2aR$^{-/-}$ (n=5) mice was compared by injecting mice with a combination of D-galactosamine (Sigma, St. Louis, Mo.) and TNF-α (PharMingen, San Diego, Calif.). D-galactosamine (700 mg/kg) was injected intraperitoneally 30 minutes before i.v. injection of recombinant mouse TNF-α (4-15 μg/kg). After six hours, mice were sacrificed and the liver damage was evaluated by measuring serum ALT levels as described in EXAMPLE 1. As shown in FIG. 3B, deficiency in A2a receptors did not affect the susceptibility of hepatocytes to in vivo damage by TNF-α. Therefore, differences between A2aR$^{+/+}$ and A2aR$^{-/-}$ mice were not explained by increased susceptibility of A2aR$^{-/-}$ hepatocytes to TNF-α, since TNF-α was equally efficient in directly destroying hepatocytes in both A2aR$^{-/-}$ and A2aR$^{+/+}$ mice in vivo (FIG. 3B). Furthermore, excessive and prolonged pro-inflammatory TNF-α accumulation was observed in the serum of A2aR$^{-/-}$ mice compared to low or undetectable TNF-α levels in A2aR$^{+/+}$ mice (FIG. 3B). IFN-γ was also present at higher concentrations and for a greater duration in A2aR$^{-/-}$ mice, although levels of IL-4 were not different between A2aR$^{-/-}$ and A2aR$^{+/+}$ mice. Inactivation of A2a receptors in A2aR$^{+/+}$ wild type mice using the A2 receptor antagonist ZM241385, also increased inflammatory tissue damage in A2aR$^{-/-}$ mice (FIG. 4).

In summary, other cAMP-triggering Gs-coupled receptors do not appreciably compensate for the lack of A2a receptors on immune cells of A2aR$^{-/-}$ mice, as demonstrated by the increased sensitivity of A2aR$^{-/-}$ mice to Con-A. Mice with genetically inactivated adenosine receptors indeed lack functional adenosine receptors. A2aR$^{-/-}$ mice have other fully functional receptors (e.g. prostaglandin or beta-adrenergic receptors), which may function as natural down-regulators of immune response. These data demonstrate that A2a receptor gene deficient mice can be used to implicate A2a receptors as non-redundant downregulators of immune response in vivo. These data also demonstrate that the signal transduction pathway leading to cAMP accumulation in these mice is functional, thereby completely excluding any possibility that an artifactual mutation exists in A2aR gene deficient mice.

Example 4

Inactivation of A2a Receptors In Vivo Exacerbates Liver Damage

This example provides methods that were used to demonstrate the tissue-protecting properties of A2 adenosine receptors in other models of inflammatory liver injury and systemic inflammation. These results demonstrate that targeted tissue damage can be achieved in vivo, for example when the targeted tissue is a tumor, the first agent or drug is specific immune cell (e.g. T cells or NK-T cells), a toxin (e.g. PEA) or a cytotoxic agent (e.g. carbon tetrachloride).

B6 mice (n=5) were injected with 12.5 mg/kg of Con-A alone or in combination with A2aR antagonist ZM241385 (2 mg/kg). *Pseudomonas* Exotoxin A (PEA, 100 μg/kg i.v., Sigma, St. Louis, Mo.) was also used to induce liver injury as follows. Mice were injected with PEA alone (n=6) or in combination with an i.p. injection of ZM241385 (n=7) before and 12 hours after the PEA injection. Carbon tetrachloride ($CCl_4$)-induced hepatotoxicity was determined by injecting (i.p.) A2aR$^{+/+}$ (n=7) and A2aR$^{-/-}$ (n=7) mice with $CCl_4$ (0.5 ml/kg, Sigma) dissolved in olive oil.

Subsequent to the injections, serum ALT measurements were made as described in EXAMPLE 1, which indicate the extent of liver damage. In addition, histological evaluations and an analysis of tissue damage and apoptotic cells (the detection of apoptotic cells by in situ staining of single strand breaks in nuclear DNA) were determined.

Figure 4A:
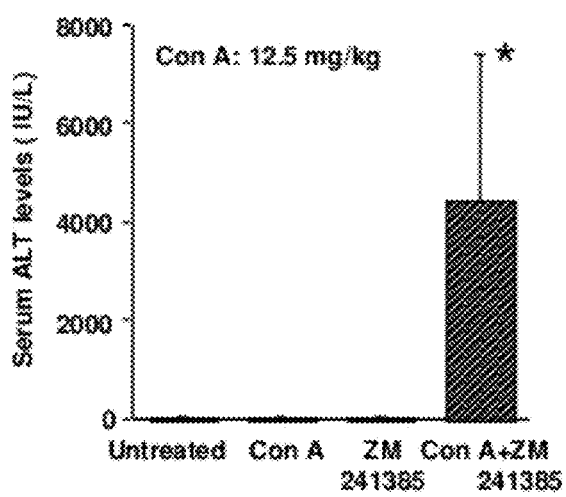
FIG. 4A is a bar graph showing serum ALT levels in mice treated with different combinations of inflammatory stimuli, (Con-A) and A2 receptor antagonist ZM241385. *P<0.05 versus A2aR$^{+/+}$ mice.
Figure 4B:
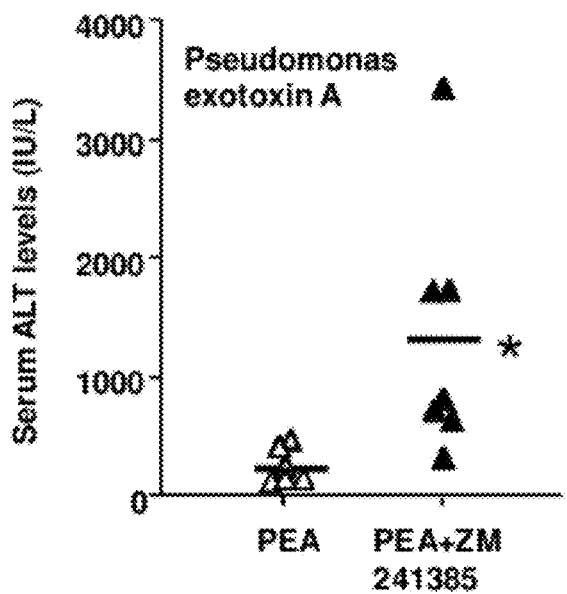
FIGS. 4B and 4C are scatter plots showing serum ALT levels in mice injected with (B) *Pseudomonas* Exotoxin A or (C) carbon tetrachloride.
Figure 4C:
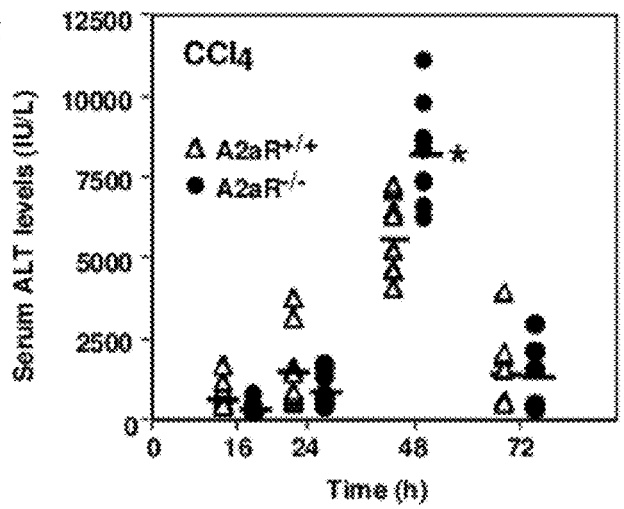
Figure 6A:
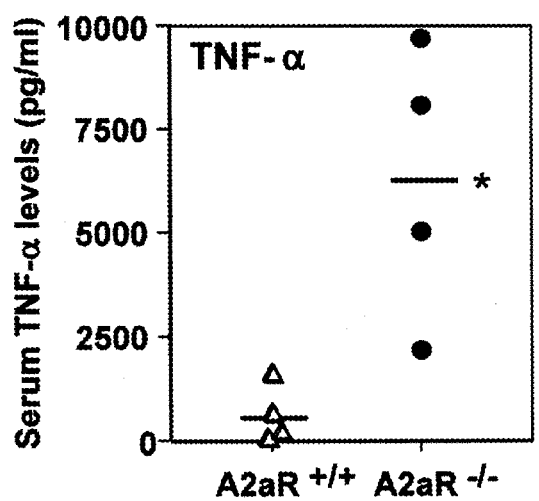
FIG. 6A-D are scatter plots showing the serum levels of the indicated cytokines in A2aR$^{-/-}$ mice as compared with A2aR$^{+/+}$ wild type mice subjected to endotoxic shock. *P<0.05.
Figure 6B:
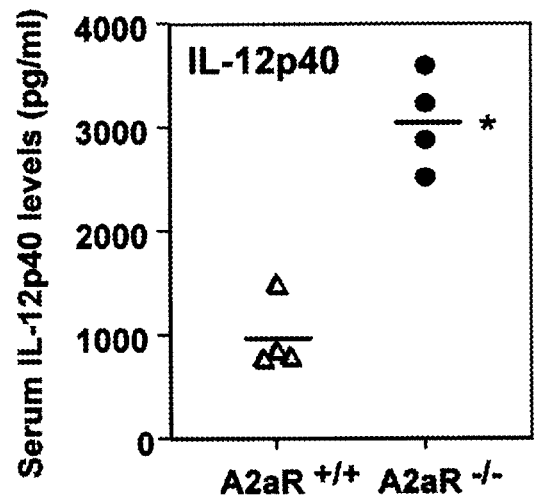
Figure 6C:
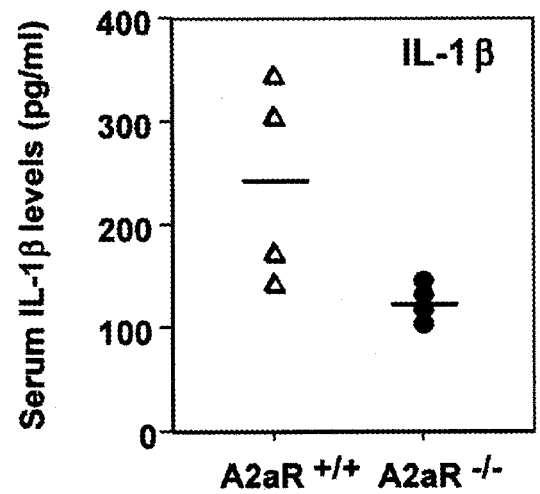
Figure 6D:
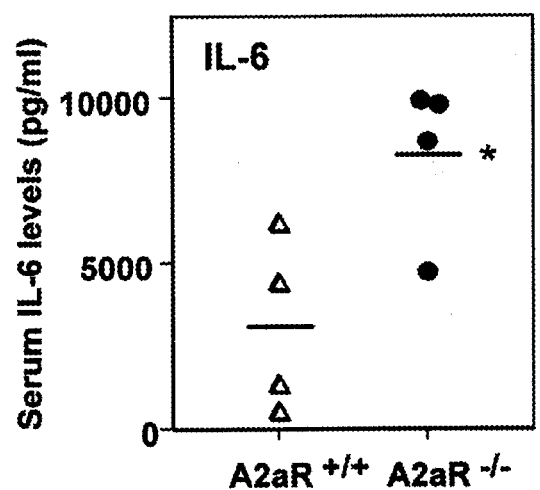

As shown in FIG. 4A, pharmacological inactivation of A2a receptors in vivo using an adenosine receptor antagonist, exacerbates Con-A-induced liver damage. Inactivation of A2 adenosine receptors in A2aR$^{+/+}$ mice by antagonist ZM241385, exacerbated the T cell- and TNF-α-dependent acute hepatotoxicity of PEA (FIG. 4B). Increased liver injury was also observed in A2aR$^{-/-}$ mice during chemically ($CCl_4$)-induced acute hepatotoxicity (FIG. 4C).

Therefore, enhanced and prolonged accumulation of pro-inflammatory cytokines and exaggerated liver damage occurs in A2a-receptor-deficient mice as compared to wild-type mice. These data demonstrate that adenosine receptors, such as A2a receptors, function in vivo as physiological downregulators of immune response/inflammation and function as protectors from excessive tissue damage. Genetic inactivation of A2a receptors results in much stronger, longer inflammatory response to very low, sub-optimal doses of pro-inflammatory stimuli. This is evidenced by tissue damage and death of animals (virtually no tissue damage and only short duration of higher levels of pro-inflammatory cytokines were detected in normal wild type littermates which express A2a receptors). Virtually no tissue damage was detected in normal wild type littermates given the same dose of pro-inflammatory stimuli, Con-A without the administration of the A2aR antagonist.

In summary, these results demonstrate that a targeted tissue (in this example it was liver, but other tumors can be targeted) can be reduced or destroyed by disengaging immunosuppressive "brakes" using two agents. The first agent is target tissue-specific, such as cytotoxic cells with tropism to a tumor, which can increase T-cell dependent tissue damage; such as an immunotoxin with tropism to a tumor (FIG. 4B, which can result in immunotoxin-dependent targeted tissue damage; and such as a toxic chemical agent with tropism to the tumor (FIG. 4C), which can result in chemotherapy-dependent targeted tissue damage. This agent initiates non-observable or low intensity inflammation. The second agent inactivates or decreases hypoxia, extracellular adenosine, and/or the presence of adenosine receptors. This second agent enhances the intensity and prolongs the duration of targeted tissue destruction.

Example 5

Enhanced Accumulation of Pro-Inflammatory Cytokines and Tissue Damage in Endotoxin-Treated A2a Receptor-Deficient Mice This example describes methods further used to demonstrate the role of A2a adenosine receptors in down-regulating pro-inflammatory cytokine accumulation and tissue damage, using an in vivo septic shock model following subcutaneous and i.v. bacterial endotoxin (LPS) injection.

Lipopolysaccharide (LPS, *E. coli* 0111:B4; 3 mg/kg, Sigma) was injected i.v. into A2aR$^{-/-}$ (n=11) and A2aR$^{+/+}$ (n=10) mice. Survival was monitored for 96-120 hours after LPS injection. Statistical analysis confirmed the higher and faster mortality of mice without adenosine receptors. As shown in FIG. 5, all A2a$^{-/-}$ mice were dead by 48-72 hours, whereas survival of A2a$^{+/+}$ mice was 10-20% at 120 hours or 96 hours.

Endotoxic shock in male A2aR$^{-/-}$ mice and age-matched A2aR$^{+/+}$ mice was induced by i.v. injection of 3 or 5 mg/kg LPS. Subsequently, at 1 hour and 16 hours after injection, blood samples were obtained by retro-orbital bleeding. In another group of mice, LPS was injected (100 μg/kg) into a dorsal air pouch, which was prepared using sterile air essentially as described in Levy et al. (*Nat. Immunol.* 2:612, 2001). Serum cytokine levels were determined at different times after LPS injection using ELISA kits obtained from R&D systems according to manufacturer's suggestions as follows: TNF-α and IL-6 levels were measured at 1 hour, and IL-12p40 and IL-1β levels at 3 hours. As shown in FIGS. 6A-D, absence of A2a adenosine receptors dramatically increases the level of pro-inflammatory cytokines in A2aR$^{-/-}$ mice as compared to wild-type mice after air pouch LPS injection (infected wound model).

Therefore, A2a adenosine receptors protect against death from septic shock, as mice lacking adenosine receptors (due to genetic inactivation), die faster (FIG. 5) and have higher levels of cytotoxic TNF-α (FIG. 6A) in response to bacterial endotoxin. These results demonstrate that A2a adenosine receptors are the natural and non-redundant "brakes" of inflammatory tissue damage.

Example 6

Enhanced Accumulation of Pro-Inflammatory Cytokines mRNA in A2aR$^{-/-}$ Mice after Activation of Immune Cells Mutant (A2aR$^{-/-}$) or wild-type mice were injected (i.p.) with 20 nmol CpG oligonucleotide (5'-T*C*CATGACGTTCCTG*A*T*G*C*T-3', asterisk means phosphorothioate. SEQ ID NO. 1). This toll-receptor activating CpG DNA preparation stimulates the immune system. After one hour, mRNA was extracted from spleenocytes and analyzed for cytokine gene expression using an RNase protection assay with commercial templates (mCK-2b and mCK-3b, Pharmingen, San Diego, Calif.).

Figure 7:
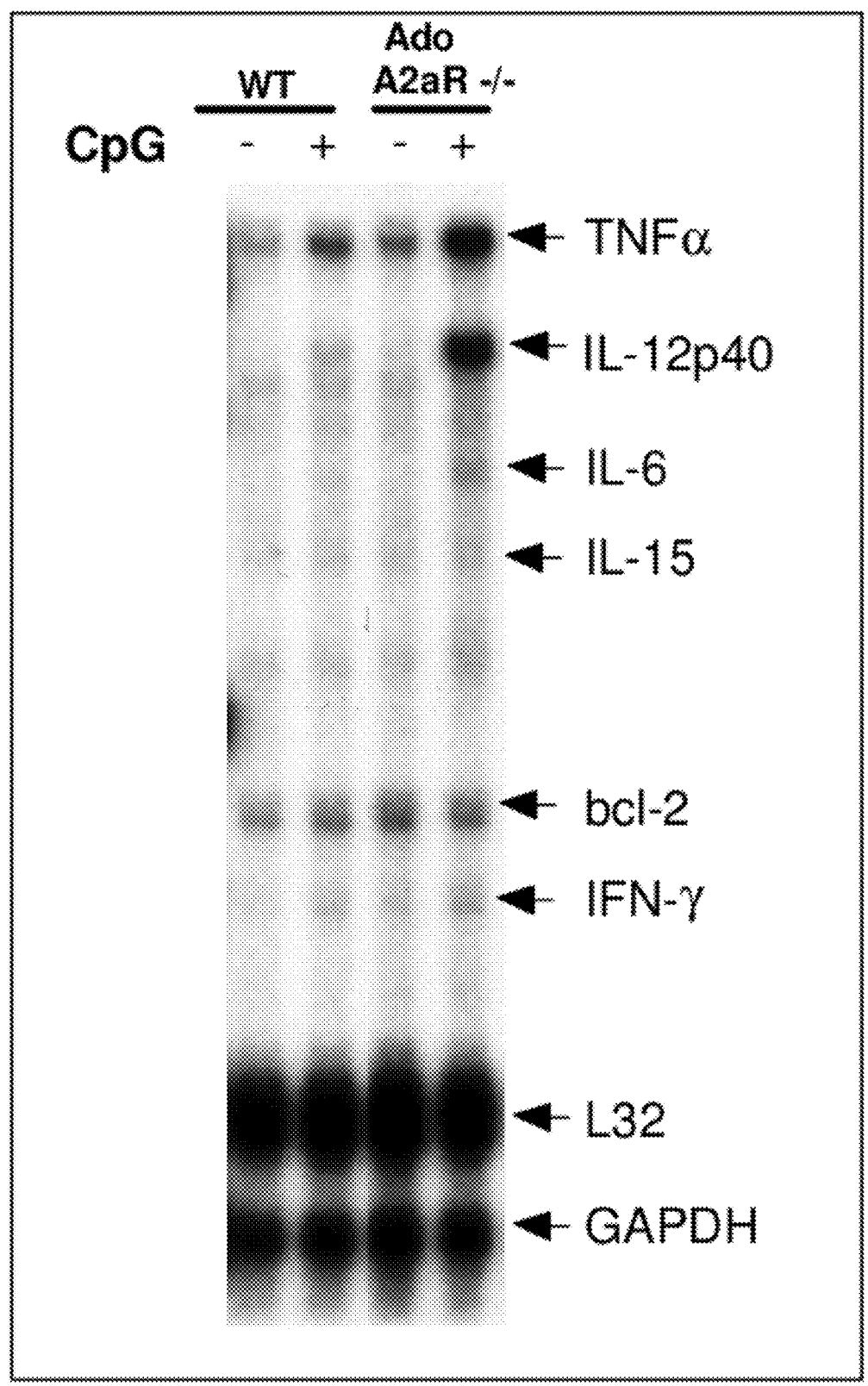
FIG. 7 is a digital image showing the results of a ribonuclease protection assay (RPA) demonstrating the increase of inflammation (by pro-inflammatory cytokines mRNA expression) in mice with inactivated A2a receptors, after treatment with inflammatory stimuli.

As shown in FIG. 7, NF-kB transcribed cytokine mRNAs (such as TNF-α and IL-12p40) are dramatically increased in the absence of adenosine receptors. Therefore, A2a adenosine receptors are involved in down-regulating pro-inflammatory cytokine mRNA accumulation including IL-12 (which is important for the T cell response), during in vivo activation of immune cells by CpG. This provides further evidence that targeted inactivation of adenosine receptors can be used to enhance the immune response. Since cytokine IL-12 is important in promoting T-cell dependent immune response, these data demonstrate that genetic targeting the "adenosine accumulation→adenosine→adenosine receptors→signaling" pathway in immune cells can enhance an immune response, which can be used as an immunoenhancer to improve vaccines.

Example 7

Adenosine Receptor Antagonists Increase Expression of Inflammatory Cytokines in CpG-Activated Immune Cells In Vivo This example describes methods used to determine the role of adenosine receptor antagonists on NF-KB activity and expression of inflammatory cytokines such as TNF and IL-12p40.

C57BL/6 mice were pretreated with ZM241385 (10 mg/kg i.p.) 15 minutes before administration of SEQ ID NO: 1, and the expression of cytokine mRNA in the spleen was compared with the mice treated with CpG alone, using the methods described in EXAMPLE 6.

Figure 8A:
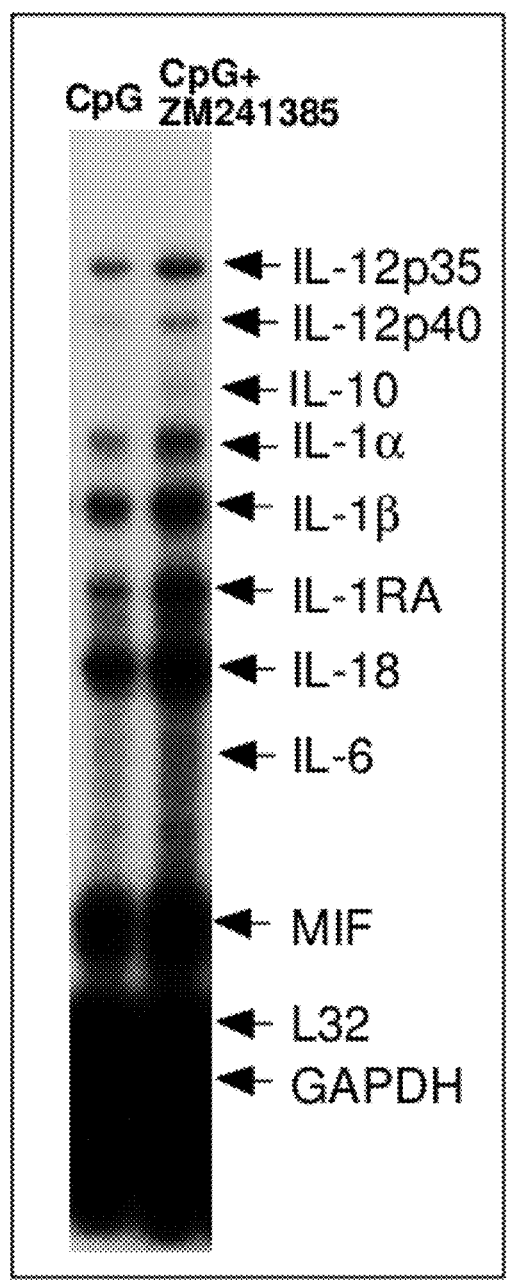
FIGS. 8A and 8B are digital images showing a ribonuclease protection assay (RPA) demonstrating the increase of inflammation (by pro-inflammatory cytokines mRNA expression) in mice with pharmacologically inactivated A2a receptors after treatment with inflammatory stimuli.
Figure 8B:
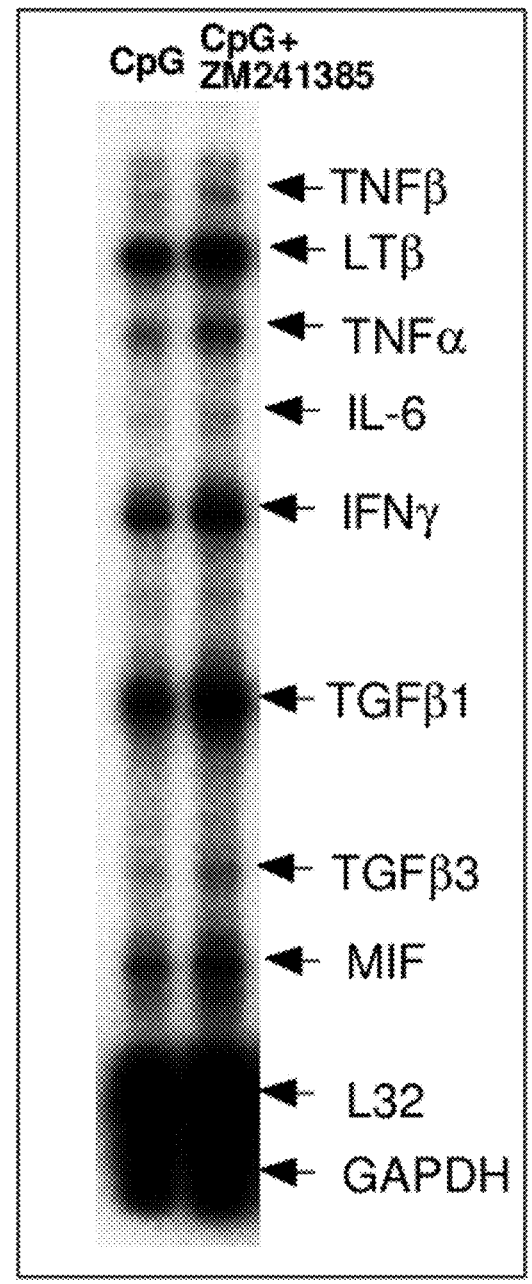

As shown in FIG. 7, in the adenosine receptor mutant mice (adenosine receptors genetically inactivated), there was higher mRNA expression of NF-kB-regulated pro-inflammatory cytokines (TNF$\alpha$, IL-12p40). Similarly, as shown in FIGS. 8A and 8B, higher expression of NF-kB-regulated pro-inflammatory cytokines is observed in ZM241385-treated mice (adenosine receptors pharmacologically inactivated). Therefore, administering an adenosine receptor antagonist can be used to increase or enhance the transcription of pro-inflammatory cytokines following CpG activation, due to enhanced or increased NF-kB activity.

Example 8

Adenosine Receptors Decrease NF-kB Nuclear Translocation and Cytokine mRNA Transcription by Inhibiting IKK-Mediated Phosphorylation of IkB To further demonstrate the role of adenosine receptors on IKK-mediated phosphorylation, which is necessary for NF-kB nuclear translocation, which is needed for expression of cytokines, the following methods were used.

Mutant (A2aR$^{-/-}$) and wild-type mice were injected (i.v.) with CpG to activate immune cells as described in EXAMPLE 6. One hour after the injection, nuclear extracts from peritoneal macrophages were isolated using standard methods. Nuclear extracts were compared in electrophoretic mobility shift assay (EMSA) for binding to specific DNA sequences according to routine EMSA methods, to determine the extent of NF-kB translocation into the nucleus of macrophages.

As shown in FIG. 9, CpG-induced NF-kB translocation into the nucleus is increased in the absence of adenosine A2a receptors. This demonstrates that A2a receptors negatively regulate NF-kB translocation into the nucleus, and thereby its activity, in vivo.

To determine the role of IkB phosorylation, C57BL/6 mice were administered (i.v.) 5 nMol of CpG (SEQ ID NO: 1) in the presence or absence of the adenosine receptor agonist CGS21680 (2 mg/kg). After 20 minutes, macrophages were isolated as described above, and subjected to Western blot analysis using Ab that recognize IkB and Ab can distinguish the phosphorylated form of IkB (IkB-P). As shown in FIG. 11A, phosphorylation of IkB was decreased or inhibited in the presence of the adenosine receptor agonist CGS21680, following immune stimulation with CpG. As shown in FIG. 11B, in control panels the parallel samples had similar levels of IkB as shown in Western blots.

Therefore, NF-kB activity is regulated by adenosine receptors due to the inhibition of (or decrease of) phosphorylation of IkB by IKK. In the absence of phosphorylation of IkB, NF-kB cannot translocate into the nucleus, and therefore NF-kB cannot induce mRNA expression of inflammatory cytokines such as IL-12p40 and TNF-$\alpha$. Enhancement of NF-kB transcription factor nuclear translocation by inhibition of A2 adenosine receptor-mediated signaling is explained by prevention of cAMP-induced inhibition of phosphorylation of IkB by IKK.

Figure 11:
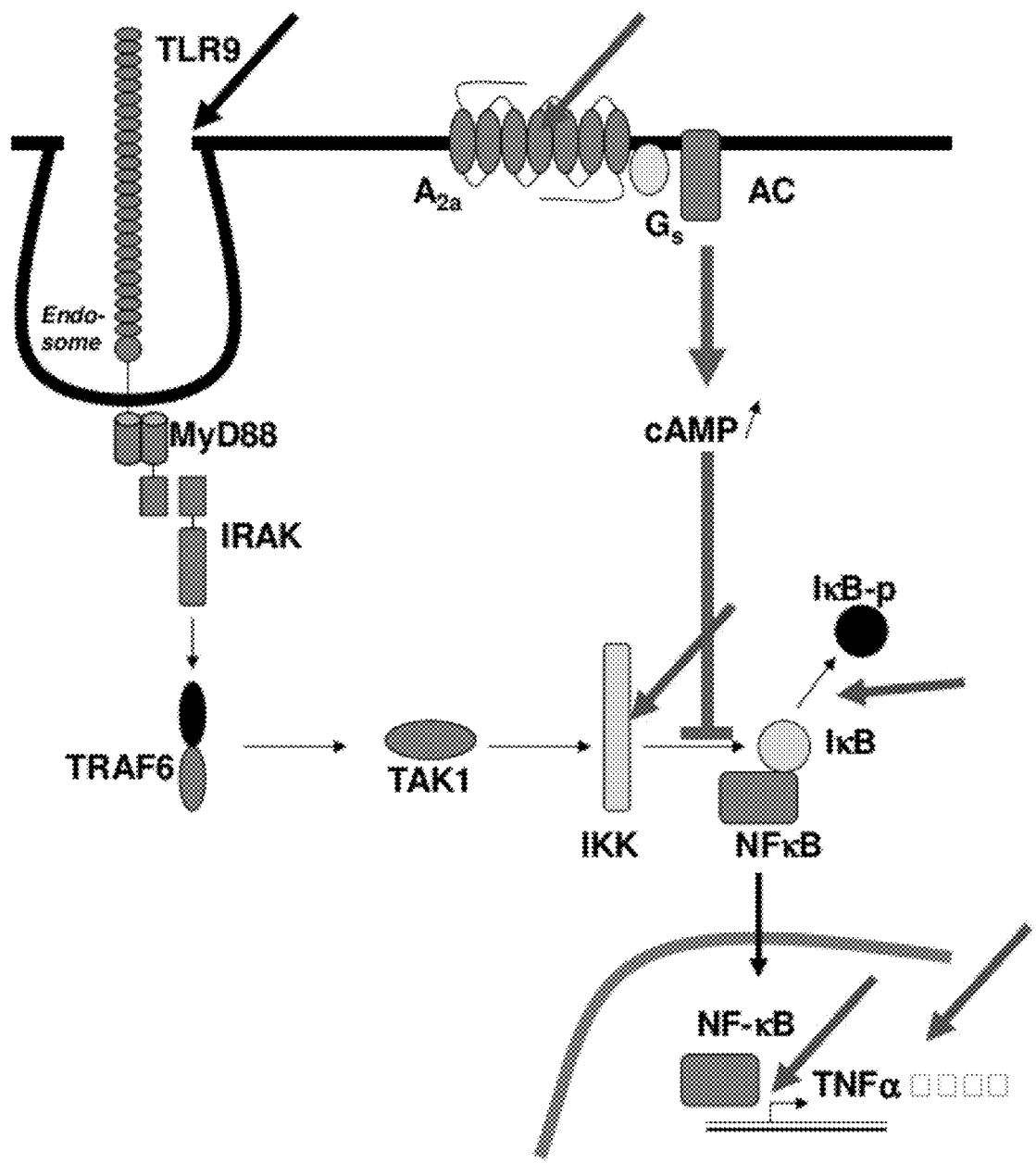
FIG. 11 is a schematic showing the intracellular events following the activation of immune cells and the mechanism of A2a adenosine receptor and cAMP-mediated inhibition of NF-kB activities.

As summarized in FIG. 11, the presence of active adenosine receptors, such as A2a, decreases or inhibits inflammation by blocking IKK-mediated IkB phosphorylation, and NF-kB nuclear translocation, thereby inhibiting or decreasing mRNA expression of pro-inflammatory cytokines.

Example 9

Adenosine Receptor Antagonists Decrease Tumor Growth

To determine if a tumor self-protection mechanism could be defeated by reducing the presence of adenosine, the following methods were used. Because tumors are hypoxic, and hypoxia is conducive to adenosine accumulation in the brain, heart, and in solid tumors, it is possible that adenosine inhibits or prevents anti-tumor immune cells (such as T-killer cells) from contacting the tumor, thus preventing the tumor from being acted upon by the anti-tumor cells. For example, the presence of adenosine may inhibit or decrease the signaling of CTL chemokines receptors (which may result in a decreased attraction to a tumor and/or a decrease or inhibition of chemotaxis); inhibit or decrease motility of CTLs; inhibit or decrease production of inflammatory cytokines by CTL; inhibit or decrease the formation of CTL/tumor conjugates; inhibit or decrease FasL/granule exocytosis; and/or inhibit or decrease a lethal hit by CTL. As a result, if adenosine is blocked or reduced, then anti-tumor cells may be more effective in reducing a tumor.

BALB/c mice were inoculated i.v. with CMS4 tumor cells (Methylcholanthrene-induced sarcoma, 2.5×10$^5$ cells) on day zero to induce the formation of lung tumors. Ten-days later, antigen-specific T-killer cells (CTL) cells (5×10$^5$ or 1×10$^6$ cells) were injected into the mice (i.v.) in the presence or absence of an i.p. injection of ZM241385 (10 mg/kg/day) or administered a relatively nonselective antagonist of A2a and A2b receptors, 1,3,7-thrimethylxantine (caffeine, 0.1% w/v) via drinking water to inactivate A2 Receptors on the CTL-cell surface, since it is through these receptors the tumor signals T-killer cells and thereby stop them from delivering the lethal "hit" to tumor cells. The lung tumors were subsequently examined on days 17, day 18 and day 24, by sacrificing the mice and evaluating their lungs for the number and size of metastasis by visual inspection.

Figure 12A:
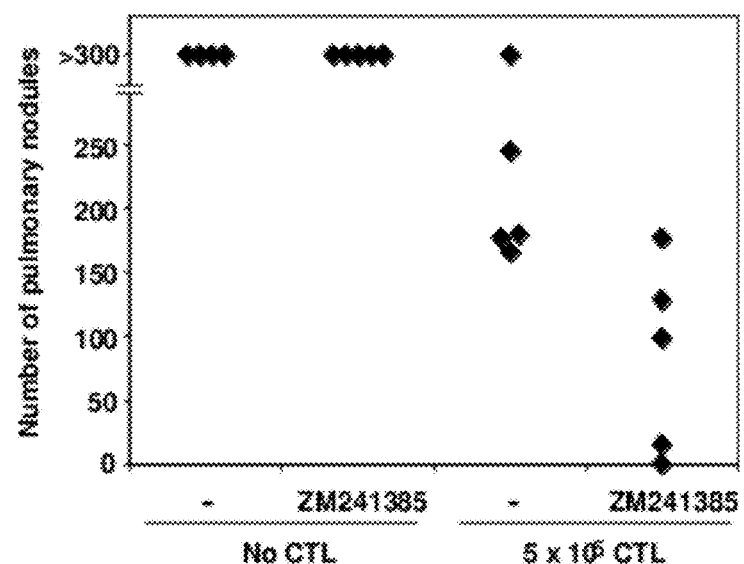
FIGS. 12A-12C are dot plots showing that adenosine receptor antagonists improve immunotherapy of cancer tumors by reducing the number of metastatic nodules.
Figure 12B:
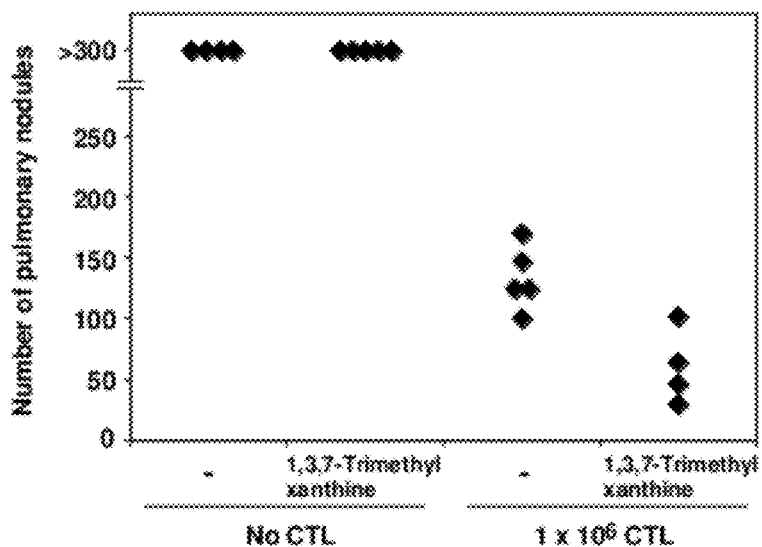
Figure 12C:
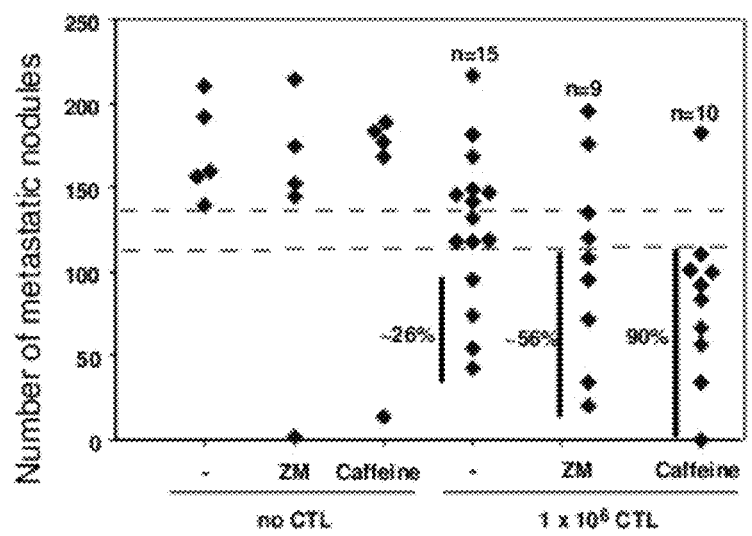

As shown in FIGS. 12A-C, administration of an adenosine receptor antagonist, such as ZM241385 or caffeine, greatly improves immunotherapy of cancer tumors, as evidenced by a decrease in the number of metastatic nodules in the lung. In contrast, CTL cells alone were not as capable of efficiently reducing tumor metastasis.

To demonstrate that similar results are obtained with non-immunogeneic tumors, such as breast tumors, the following methods were used. BALB/c mice were inoculated subcutaneously with 1×10$^5$ non-immunogeneic 4T1 breast tumor cells (American Type Culture Collection, Manassas, Va., Catalog No. CRL-2539) on day zero to induce the formation of breast tumors. When injected into BALB/c mice, 4T1 cells spontaneously produce highly metastatic tumors that can metastasize to the lung, liver, lymph nodes and brain while the primary tumor is growing in situ. Seven days after tumor inoculation, mice were injected daily (i.p.) with ZM241385

(10 mg/kg) or caffeine (20 mg/kg). Time-dependent changes of tumor diameter and tumor volume were subsequently calculated.

Figure 13:
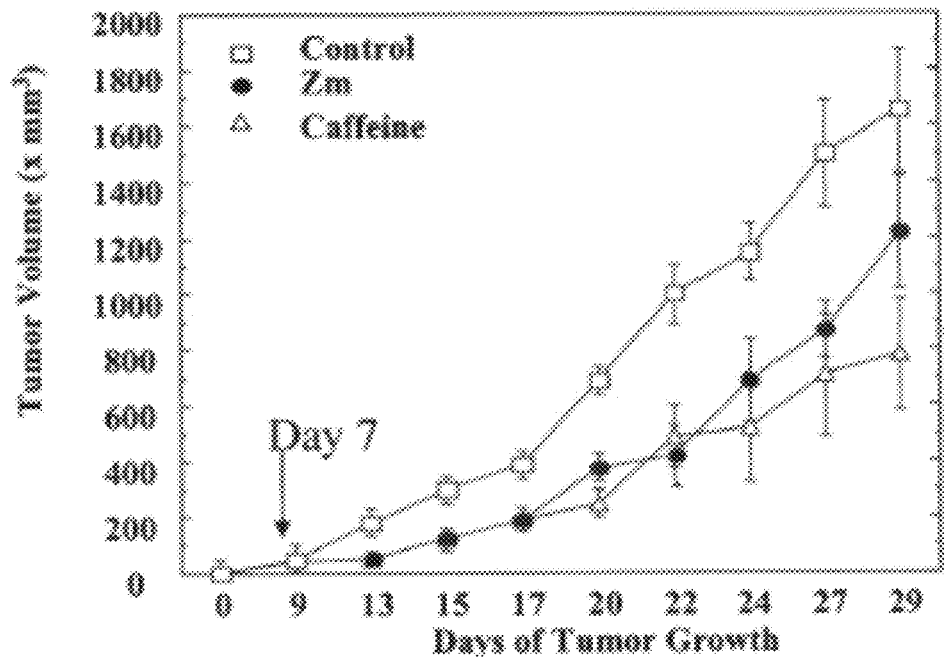
FIGS. 13 and 14 are graphs showing that adenosine receptor antagonists improve the therapy of cancers by reducing the size/volume of tumors.

As shown in FIG. 13, adenosine receptor antagonists slow the growth of non-immunogeneic 4T1 breast tumor cells (s.c.), indicating that administration of an adenosine receptor antagonists to a subject having a tumor can reduce the number and/or size of one or more tumors in the subject. These results also indicate that adenosine receptor antagonists reduce tumor growth by impairing angiogenesis.

Example 10

Adenosine Receptor Antagonists Decrease Tumor Size

This example describes methods that were used to improve anti-tumor vaccination by co-administering an adenosine receptor antagonist.

BALB/c mice (immunocompromised nude mice; or immunocompetent C57BL/6 mice) were inoculated subcutaneously with B16 melanoma cells (American Type Culture Collection, Manassas, Va.), or B16-H2-Kd transfected tumor cells (increases the immunogenicity of the cells) on day zero to induce the formation of melanomas. The treatment with adenosine receptor antagonists started 28 days after injection of tumor cells, when the tumor reached 7-9 mm in diameter.

Figure 14:
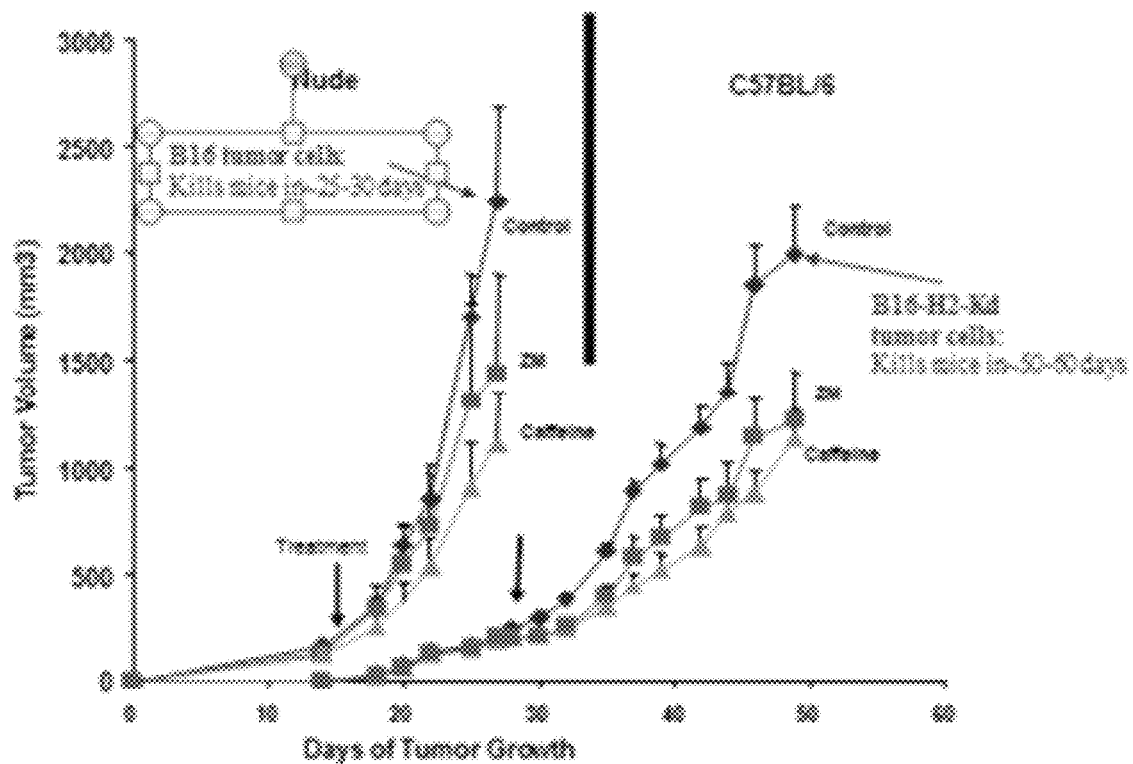

As shown in FIG. 14, daily i.p. treatments with ZM241385 (0.2 mg/mouse) and caffeine (0.4 mg/mouse) resulted in tumor retardation that became significant after 3-7 days of treatment. The delay in tumor growth was greater in immunocompetent C57BL/6 mice, and less so in immunocompromised nude mice. However, as the tumor increases in size, both antagonists slow down tumor growth even in immunocompromised animals. This indicates that administration of adenosine receptor antagonists to a subject having a tumor can reduce the number and/or size of one or more tumors in the subject. In addition, adenosine receptor antagonists appear to improve both anti-tumor immunity and preventing or decreasing angiogenesis.

Example 11

Adenosine Receptor Antagonists Improve Immune Response to Subcutaneous and Intra-Peritoneal Vaccination This example describes methods used to determine if an immune response to vaccines can be improved by co-administering an adenosine receptor antagonist, such as A2a and A3 antagonists, and whether any effects is altered if the vaccine is delivered via different delivery routes.

TNP-KLH (100 µg, Sigma), a model antigen, was injected i.p. or subcutaneously into the footpad of A2aR$^{+/+}$ mice along with an adenosine receptor antagonist (about 1 mg/kg of theophylline (an A2a antagonist), ZM241385 (an A2a antagonist), or MRS1220 (an A3 antagonist, Sigma)). The antigen was prepared for injection as follows. DNP-KLH (1.0 mg/ml, Biosearch Technologies, Inc. catalog no. T-5060-5) was prepared in PBS (e.g. dissolve 4.0 mg of purified DNP-KLH in PBS and raise volume to 4.0 ml). Complete Freund's Adjuvant (2.0 ml, CFA; Sigma F-5881) was vortexed and mixed with 2.0 ml of the TNP-KLH solution at 4° C. The CFA/KLH mixture was drawn into a 3-ml glass syringe with a 19-gauge needle. The syringe was attached to a double-ended locking hub connector or a plastic 3-way stopcock. An empty 2-ml glass syringe was attached to the other end and the mixture forced back and forth from one end to the other repeatedly. When the mixture was white and homogeneous, the connector or stopcock was disconnected, a 25 gauge needle attached, and tested for emulsion by placing a drop on the surface of 50 ml of cold water in a 100-ml beaker. The drop should hold together; if not, repeat mixing. 200 µl (100 µg) was injected intraperitoneally (i.p.) into each mouse.

Samples of blood were obtained by retro-orbital bleeding at 7, 14, and 21 days after TNP-KLH and theophylline injection. Serum levels of anti-TNP-specific IgG1, IgG2a, IgG2b, IgG3, and IgM were estimated using an ELISA kit (Sigma) according to the manufacturer's instructions.

Serum levels of anti-TNP-specific IgG1 were markedly increased at seven days in mice co-injected with TNP-KLH and ZM241385 or MRS1220, as compared to control. $IgG_2$ was also improved on day 7. Therefore, blocking the endogenous anti-inflammatory pathway using adenosine receptor antagonists improves immune response to vaccination (as evidenced by higher titers of antigen-specific immunoglobulin $IgG_1$), when adenosine receptor antagonists are administered with a vaccine.

Figure 15:
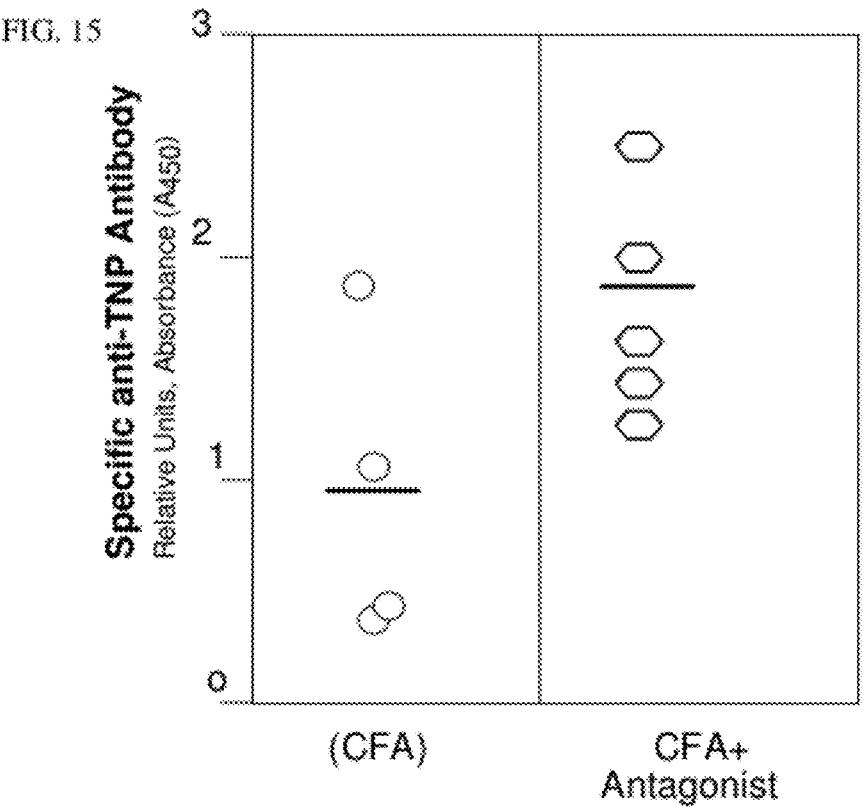
FIG. 15 is a scatter plot showing IgG$_1$ concentration in mice injected subcutaneously with TNP-KLH alone (CFA) or with adenosine receptor antagonist theophylline (CFA+antagonist) and demonstrates the improvement of antibody production by theophylline in the immunization mixture.

Similarly, serum levels of anti-TNP-specific IgG1 were markedly increased at seven days in mice co-injected i.p. (FIG. 15) or subcutaneously with TNP-KLH and theophyllin, as compared to control. Therefore, co-administration of an adenosine receptor antagonist with a vaccine potentiates the immune response to the vaccine, when vaccination is intraperitoneal or subcutaneous. Pharmacological inactivation of adenosine receptors, such as A2a and A3, using antagonists results in higher titers of antigen-specific immunoglobulins $IgG_1$, which such antagonists are administered with a vaccine.

Example 12

Administration of Adenosine Receptor Antagonists with Anti-Cancer Agents

This example describes methods that can be used to facilitate the treatment of cancer in a subject using one or more adenosine receptor antagonists, alone or in combination with anti-cancer agents. This protocol serves as an example of such a treatment method, and is not limiting. Those of skill in the art can modify the protocol to suit the needs of the subject, and to optimize for the particular agents used. Subjects can, but need not, have received previous chemo-radio- or gene therapeutic treatments. Optimally, the patient will exhibit adequate bone marrow function (defined as peripheral absolute granulocyte count of >2,000/mm$^3$ and platelet count of 100,000/mm$^3$.

Adenosine receptor antagonists are administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques. Adenosine receptor antagonists can be administered in dosages of about 0.1 mg/kg to about 1 g/kg, depending on the antagonist used. For example, adenosine receptor antagonists can be administered to a subject at a dose of at least 0.5 mg/kg of body weight, such as 3-10 mg/kg. The adenosine receptor antagonists can be delivered to the patient before, after or concurrently with the other anti-cancer agents.

A typical treatment course can include about six doses delivered over a 7 to 21 day period. Alternatively, a treatment course can include daily doses delivered over a 7 to 21 day period. Upon election by the clinician, the regimen can be continued six doses every three weeks or on a more frequent (daily, twice daily, four times a day, etc.) or less frequent (monthly, bimonthly, quarterly, etc.) basis. Of course, these are only exemplary times for treatment, and the skilled practitioner will readily recognize that many other time-courses are possible. The adenosine receptor antagonists can be combined with any of a number of conventional chemotherapeutic regimens.

Regional delivery of adenosine receptor antagonists is an efficient method for delivering a therapeutically effective dose to counteract the clinical disease. Likewise, the chemotherapeutic agents can be directed to a particular affected region. Alternatively, systemic delivery of either or both agents can be appropriate.

Clinical responses can be defined by an acceptable measure. For example, a complete response can be defined by the disappearance of all measurable disease for at least a month. A partial response can be defined by a 20% or greater, such as 50% or greater, such as 75% or greater, reduction of the sum of the products of perpendicular diameters of all evaluable tumor nodules or at least 1 month with no tumor sites showing enlargement. Similarly, a mixed response can be defined by a reduction of the product of perpendicular diameters of all measurable lesions by 20% or greater, such as 50% or greater, with progression in one or more sites.

able carriers, adjuvants, and vehicles as desired. Adenosine receptor antagonists can be administered in dosages of about 0.1 mg/kg to about 1 g/kg, depending on the antagonist used. The adenosine receptor antagonists can be delivered to the patient before, after or concurrently with the vaccine.

A typical vaccination course can comprise a single dose. Optionally, the course can be repeated every twelve weeks or on a more frequent (monthly, weekly, etc.) or less frequent (biannually, annually, every three years, every ten years, etc.) basis. Of course, these are only exemplary times for vaccination, and the skilled practitioner will readily recognize that many other time-courses are possible. The adenosine receptor antagonists can be combined with any of a number of conventional vaccines.

Clinical responses can be defined by an acceptable measure. For example, TNF-α, IFN-γ, IL-4, IL-6, IL-1β and IL-12p40 levels in blood or serum samples can be determined using commercially available ELISA kits according to manufacturer suggestions. Alternately, antibodies to the vaccine can be measured in blood or serum samples using ELISA kits.

Of course, the above-described treatment regimes can be altered by those of skill in the art. In view of the many possible embodiments to which the principles of our disclosure may be applied, it should be recognized that the illustrated embodiments are only examples of the disclosure and should not be taken as a limitation on the scope of the disclosure. Rather, the scope of the disclosure is defined by the following claims. We therefore claim as our invention all that comes within the scope and spirit of these claims.

```
                            SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: CpG oligonucleotide.  Phosphorothioate linkages
      between nucleotides 1 and 2; 2 and 3; 15 and 16; 16 and 17; 17 and
      18; 18 and 19; 19 and 20.

<400> SEQUENCE: 1
tccatgacgt tcctgatgct                                                     20
```

Of course, the above-described treatment regimes can be altered by those of skill in the art, who will be able to take the information disclosed in this specification and optimize treatment regimes.

Example 13

Using Adenosine Receptor Antagonists as an Adjuvant

This example describes a protocol for using one or more adenosine receptor antagonists as an adjuvant by administering the adenosine receptor antagonist to a subject in combination with a vaccine. This protocol is intended to serve as an example of such a method, and is not limiting. Those of skill in the art will be able to modify the protocol to suit the needs of the subject, and to optimize for the particular antagonists and vaccines used.

Adenosine receptor antagonists are administered orally, topically, or parenterally in dosage unit formulations containing standard, well known non-toxic physiologically accept-

We claim:

1. A method for enhancing an immune response in a subject to an antigenic polypeptide, comprising:
   administering to the subject an antigenic polypeptide; and
   administering to the subject a therapeutically effective dose of an adenosine A2a receptor antagonist and/or an inhibitor of extracellular adenosine, wherein the adenosine A2a receptor antagonist and/or an inhibitor of extracellular adenosine enhances an immune response stimulated by the antigenic polypeptide.

2. The method of claim 1, wherein the adenosine A2a receptor antagonist is ZM241385 (4-(2-[7-amino-2-(2-furyl)[1,2,4]triazolo[2,3-α][1,3,5]triazin-5yl-amino]ethyl)phenol), 1,3,7-trimethylxanthine (caffeine), theophylline, theobromine, SCH 58261, or KW-6002.

3. The method of claim 1, wherein the adenosine A2a receptor antagonist is ZM241385 (4-(2-[7-amino-2-(2-furyl)[1,2,4]triazolo[2,3-α][1,3,5]triazin-5yl-amino]ethyl)phenol), 1,3,7-trimethylxanthine (caffeine), or KW-6002.

4. The method of claim 1, wherein the inhibitor of extracellular adenosine is an oxygenation agent, a redox-potential changing agent, adenosine deaminase, adenosine kinase, ADA-PEG, oxygenation of the subject, or combinations thereof.

5. The method of claim 1, wherein the antigenic polypeptide is a viral antigenic polypeptide.

6. The method of claim 1, wherein the antigenic polypeptide is a bacterial antigenic polypeptide.

7. The method of claim 5, wherein the viral antigenic polypeptide is present in a live, attenuated, or heat killed vaccine.

8. The method of claim 1, wherein enhancing the immune response comprises increasing an activity of an immune cell in the subject.

9. The method of claim 8, wherein the immune cell is a cell that produces one or more pro-inflammatory cytokines.

10. The method of claim 8, wherein the immune cell is a macrophage, granulocyte, monocyte, neutrophil, dendritic cell, T cell, B cell, or natural killer cell.

11. The method of claim 10, wherein the immune cell is a B cell and wherein the activity is antibody production.

12. The method of claim 10, wherein the immune cell is a macrophage, granulocyte, monocyte, or dendritic cell, and wherein the activity is pro-inflammatory cytokine production.

13. The method of claim 1, wherein enhancing the immune response comprises increasing antigen-specific antibody titers in the subject.

14. The method of claim 1, wherein the immune response is a pro-inflammatory cytokine response.

15. The method of claim 14, wherein the pro-inflammatory cytokine response is an increase in IL-12p40 and/or TNF-α mRNA expression.

16. The method of claim 1, wherein the subject is immunocompromised.

17. The method of claim 16, wherein the subject is infected with an immunodeficiency virus.

18. The method of claim 17, wherein the immunodeficiency virus is HIV-1 or HIV-2.

19. The method of claim 16, wherein the subject is receiving immunosuppressive therapy.

20. The method of claim 1, further comprising administering an adjuvant to the subject.

21. The method of claim 6, wherein the subject is a mammalian subject infected with a bacterial pathogen.

22. The method of claim 5, wherein the subject is a mammalian subject infected with a viral pathogen.

* * * * *